United States Patent [19]
Hirschbein et al.

[11] Patent Number: 5,859,233
[45] Date of Patent: Jan. 12, 1999

[54] SYNTHONS FOR SYNTHESIS OF OLIGONUCLEOTIDE N3-P5 PHOSPHORAMIDATES

[75] Inventors: Bernard L. Hirschbein, San Francisco; Karen L. Fearon, Union City; Sergei M. Gryaznov; Sarah N. McCurdy, both of San Mateo; Jeffrey S. Nelson; Ronald G. Schultz, both of Fremont, all of Calif.

[73] Assignee: Lynx Therapeutics, Inc., Hayward, Calif.

[21] Appl. No.: 771,789

[22] Filed: Dec. 20, 1996

Related U.S. Application Data

[63] Continuation-in-part of Ser. No. 663,918, Jun. 14, 1996, which is a continuation-in-part of Ser. No. 603,566, Feb. 21, 1996, Pat. No. 5,684,143.

[51] Int. Cl.$^6$ ............................. C07H 19/10; C07H 19/20
[52] U.S. Cl. .................. 536/26.1; 536/26.12; 536/26.14
[58] Field of Search ............................. 536/25.32, 26.1, 536/26.12, 26.14

[56] References Cited

U.S. PATENT DOCUMENTS 5,476,925  12/1995  Letsinger et al. ...................... 536/23.1

FOREIGN PATENT DOCUMENTS 2077314   3/1993  Canada .
0490281 A1  6/1992  European Pat. Off. .
0552766 A2  7/1993  European Pat. Off. .
4129318 A1  9/1991  Germany .

OTHER PUBLICATIONS

Abraham, et al., "A Phosphoramidite–Based Synthesis of Phosphoramidate Amino Acid Diesters of Antiviral Nucleosides," *Nucleosides & Nucleotides* 13: 1891–1903 (1994).
Agrawal, et al., "Oligodexoynucleoside Phosphoramidates and Phosphorothioates as Inhibitors of Human Immunodeficiency Virus," *Proc. Natl. Acad. Sci. USA* 85: 7079–7083 (1988).
Azhayev, et al., "Synthesis of Phosphoramidate Analogs of Ribonucleoside Phosphates," *Coll. Czechoslov. Chem. Commun.* 44: 792–798 (1979).
Azhayev, et al., "Aminonucleosides and Their Derivatives. IX. Synthesis of Short Oligoribonucleotide with Phosphoramide Internucleotide Bonds,"*Bioorganicheskaya Khimiya* 8: 1218–1224 (1982). [translation attached].
Azhayev, et al., "Synthesis of Phosphoramidate Analogues of Short Oligoribunucleotides," *Nuc. Acids Res., Symp. Series* 9:251–254 (1981).
Bannwarth, "166. Solid–Phase Synthesis of Oligodeoxynucleotides Containing Phosphoramidate Internucleotide Linkages and Their Specific Chemical Cleavage," *Helvetica Chim. Acta* 71: 1517–1527 (1989).
Chen, et al., "Synthesis of Oligonucleotides N3'→P5' Phosphoramidates," *Nuc. Acids Res.* 23:2661–2668 (1995).
Gryaznov and Letsinger, "Synthesis and Properties of Oligonucleotides Containing Aminodeoxythymidine Units," *Nuc. Acids Res.* 20:3403–3409 (1992).
Gryaznov and Chen, "Oligonucleotide N3'→N5' Phosphoramidates: Synthesis and Hybridization Properties," *J. Am. Chem. soc.* 116:3143–3144 (1994).
Gryaznov, et al., "Oligonucleotide N3'→N5' Phosphoramidates," *Proc. Natl. Acad. Sci. USA* 92:5798–5802 (1995).
Herdewijn, et al., "Synthesis and Biological Activity of the Mono– and Diamino Analogues of 2'–Deoxyadenosine, Cordycepin, 9–(3–deoxy–β–D–threopentofuranosyl)–adenine," *Nucleosides & Nucleotides* 8: 1231–1257 (1989).
Krayevsky, et al., "Synthesis of Oligonucleotides with 5'→3' Phosphoamidoester Bond," *Nuc. Acids Res., Symp. Series No. 9*, pp. 203–205 (1981).
Mag and Engels, "Synthesis and Selective Cleavage of Oligodeoxyribonucleosides Containing Non–Chiral Internucleotide Phosphoramidate Linkages," *Nuc. Acids Res.* 17:5973–5988 (1989).
Mag, et al., "Synthesis and Selective Cleavage of an Oligodeoxynucleotide Containing a Bridged Non–Chiral Internucleotide 3'–Phosphoramidate Linkage," *Tetrahedron Lett.* 33:7319–7322 (1992).
Mag and Engels, "Synthesis of Dinucleotides Containing a Bridged Non–Chiral Internucleoside 5'–or 3'–phosphoramidate Linkage," *Tetrahedron* 50:10225–10234 (1994).
Robles, J., et al., "Stepwise Solid–Phase Synthesis of Nucleopeptide Phac–Ser(p$^5$' CATCAT) –Gly–Asp–OH from Adenovirus–2 Nucleoprotein," *Tetrahedron Lett.* 35:4449–4452 (1994).
Saha, et al., "Synthesis of Modified Achiral Internucleoside Linkages: –NCHCH2CH2–Linked Oligonucleosides," *Tetrahedron Lett.* 34:6017–6020 (1993).
Zaitseva, et al., "Aminonucleosides and Their Derivatives. X. 2'–deoxydinucleoside Phosphates and Deoxydinucleotides with Phosphoamidate Bonds," *Bioorganicheskaya Khimiya* 10:401–407 (1994). [translation attached].
Zielinski and Orgel, "Oligomerization of Activated Derivatives of 3'–amino–3'–deoxyguanosine on poly (C) and poly (G) Templates," *Nuc. Acids Res.* 13:2469–2484 (1985).
Zielinski and Orgel, "Autocatalytic Synthesis of a Tetranucleotide Analog," *Nature* 327:346–347 (1987).
Zielinski and Orgel, "Oligoaminonucleotide Phosphoramidates, Oligomerization of Dimers of 3'–amino–3'–deoxy–nucleotides (GC and CG) in Aqueous Solution," *Nuc. Acids Res.* 1699:1715 (1987).

Primary Examiner—Gary L. Kunz
Attorney, Agent, or Firm—Stephen C. Macevicz; Vincent M. Powers

[57] ABSTRACT

The invention provides a method of synthesizing oligonucleotide N3'→P5' phosphoramidates using an amine-exchange reaction of phosphoramidites in which a -deprotected 3'-amino group of a solid phase supported oligonucleotide chain is exhanged for the amino portion of a 5'-phosphoramidite of an incoming monomer which has a protected 3'-amino group. The resulting internucleotide phosphoramidite linkage is then oxidized to form a stable protected phosphoramidate linkage. The method of the invention greatly improves product yields and reduces reagent usage over currently available methods for synthesizing the above class of compound.

8 Claims, 5 Drawing Sheets

Crude OD's = 96
Full Length Product Purity = 42.4%

10N-Exchange HPLC of 5'-AAC-GAG-TTG-GGG-CAT-3'

Crude OD's = 70.8
Full Length Product Purity = 62%

10N-Exchange HPLC of 5'-TTC-TCT-CTC-TA-3'

SYNTHONS FOR SYNTHESIS OF OLIGONUCLEOTIDE N3-P5 PHOSPHORAMIDATES

This is a continuation-in-part of co-pending U.S. patent application Ser. No. 08/663,918 filed 14 Jun. 1996, which is a continuation-in-part of U.S. patent application Ser. No. 08/603,566 filed 21 Feb. 1996 now U.S. Pat. No. 5,684,143.

FIELD OF THE INVENTION

The invention relates generally to nucleic acid polymer chemistry, and more particularly, to methods of synthesizing oligonucleotide N3'→P5' phosphoramidates.

BACKGROUND

Nucleic acid polymer chemistry has played a crucial role in many developing technologies in the pharmaceutical, diagnostic, and analytical fields, and more particularly in the subfields of antisense and anti-gene therapeutics, combinatorial chemistry, branched DNA signal amplification, and array-based DNA diagnostics and analysis e.g. Uhlmann and Peyman, Chemical Reviews, 90: 543–584 (1990); Milligan et al, J. Med. Chem. 36: 1923–1937 (1993); Mesmaeker et al, Current Opinion in Structural Biology, 5: 343–355 (1995); Thuong et al, Angew. Chem. Int. Ed. Engl., 32: 666–690 (1993); Brenner et al, Proc. Natl. Acad. Sci., 89: 5381–5383 (1992); Gold et al, Ann. Rev. Biochem., 64: 763–797 (1995); Gallop et al, J. Med. Chem. 37: 1233–1258 (1994); Gordon et al, J. Med. Chem. 37: 1385–1401 (1994); Gryaznov, International application PCT/US94/07557; Urdea et al, U.S. Pat. No. 5,124,246; Southern et al, Genomics, 13: 1008–1017 (1992); McGall et al, U.S. Pat. No. 5,412,087; Fodor et al, U.S. Pat. No. 5,424,186; Pirrung et al, U.S. Pat. No. 5,405,783; and the like.

Much of this chemistry has been directed to improving the binding strength, specificity, and nuclease resistance of natural nucleic acid polymers, such as DNA. Unfortunately, improvements in one property, such as nuclease resistance, often involve trade-offs against other properties, such as binding strength. Examples of such trade-offs abound: peptide nucleic acids (PNAs) display good nuclease resistance and binding strength, but have reduced cellular uptake in test cultures, e.g. Hanvey et al, Science, 258: 1481–1485 (1992); phosphorothioates display good nuclease resistance and solubility, but are typically synthesized as P-chiral mixtures and display several sequence-non-specific biological effects, e.g. Stein et al, Science, 261: 1004–1012 (1993); methylphosphonates display good nuclease resistance and cellular uptake, but are also typically synthesized as P-chiral mixtures and have reduce duplex stability, e.g. Mesmaeker et al (cited above); and so on.

Recently, a new class of oligonucleotide analog has been developed having so-called N3'→P5' phosphoramidate internucleoside linkages which display very favorable binding properties, nuclease resistance, and solubility, Gryaznov and Letsinger, Nucleic Acids Research, 20: 3403–3409 (1992); Chen et al, Nucleic Acids Research, 23: 2661–2668 (1995); Gryaznov et al, Proc. Natl. Acad. Sci., 92: 5798–5802 (1995); and Gryaznov et al, J. Am. Chem. Soc., 116: 3143–3144(1994). Unfortunately, low synthesis yields of these compounds with published protocols has inhibited their commercial application.

The utility of this new class of oligonucleotide analog would be significantly increased if modifications and new synthesis approaches could be found that would improve synthesis yields without a concomitant loss in any other of its other favorable properties outlined above.

SUMMARY OF THE INVENTION

In view of the above, an important objective of our invention is to provide a new approach to solid phase synthesis of oligonucleotide N3'→P5' phosphoramidates in which stepwise coupling yields are significantly increased.

Another objective of our invention is to provide novel 3'-protected amino-5'-phosphoramidite monomers for use in the method of the invention.

A further objective of the invention is to provide a practical large-scale synthesis method for making oligonucleotide N3'→P5' phosphoramidates, particularly 2'-deoxyoligonucleotide N3'→P5' phosphoramidates.

These and other objects of our invention are accomplished by providing a method of synthesizing oligonucleotide N3'→P5' phosphoramidates using an amine-exchange reaction in which a deprotected 3'-amino group of a solid phase supported oligonucleotide chain is exchanged for the amino portion of a 5'-phosphoramidite of an incoming monomer which has a protected 3'-amino group. The resulting internucleotide phosphoramidite linkage is then oxidized to form a stable protected phosphoramidate linkage. The general scheme of the reaction is depicted below.

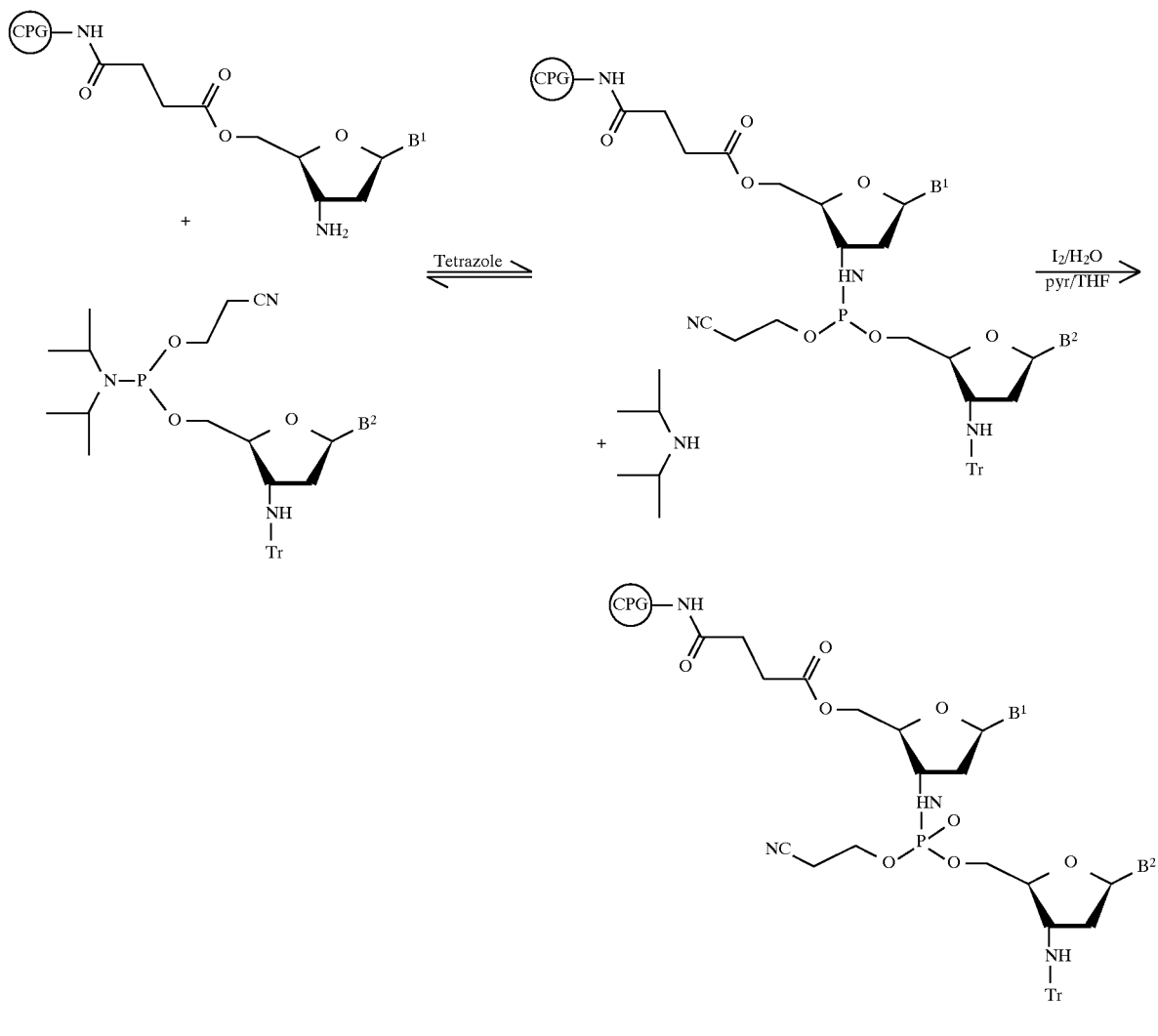

Generally, the method of the invention includes the following steps: (a) providing a first nucleoside attached to a solid phase support, the first nucleoside having a protected 3' amino group; (b) deprotecting the protected 3' amino group to form a free 3' amino group; (c) reacting the free 3' amino group with a 3'-protected aminonucleoside-5'-phosphoramidite monomer to form an internucleoside N3'→P5' phosphoramidite linkage; (d) oxidizing said linkage; and (e) repeating steps (b) through (d) until the desired oligonucleotide N3'→P5' phosphoramidate is synthesized. Preferably, the nitrogen moiety of the 5'-phosphoramidite of the 3'-protected aminonucleoside-5'-phosphoramidite monomer is a sterically hindered amine having a pKa of at least 10.

The invention further includes 3'-protected-aminonucleoside-5'-phosphoramidite monomers of the following formula, which monomers are particularly useful in the method of the invention:

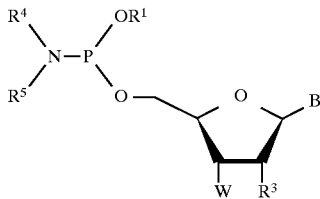

wherein: B is pyrimidine, purine, or an analog thereof; $R^1$ is a phosphate protecting group; W is either —$NHR^2$ or —$OR^7$, where $R^2$ is an amino protecting group and $R^7$ is a hydroxyl protecting group; $R^3$ is hydrogen, hydroxyl, fluoro or —OR', wherein R' is alkyl having from 1 to 3 carbon atoms or a 2'-hydroxyl protecting group, such as alkylsilyl, e.g. t-butyldimethylsilyl, or the like; and $R^4$ and $R^5$ together with the nitrogen to which they are attached form an alkylamino- or arylamino leaving group having up to 40 carbon atoms and/or heteroatoms selected from the group consisting of oxygen, sulfur, and nitrogen.

Monomers with W as —$OR^7$ are particularly useful in synthesizing chimeric oligonucleotides containing both N3'→P5' phosphoramidate linkages and other linkages, such as phosphodiester, phosphorothioate, and the like.

The invention overcomes critical shortcomings of prior art methods of synthesizing oligonucleotide N3'→P5' phosphoramidates having either fully amidated or partially amidated linkages and opens the way for commercial scale production of such compounds. In particular, the invention provides greatly increased coupling yields using much lower molar equivalents of monomer reactants which, in turn, allows commercially feasible synthesis of the oligonucleotide N3'→P5' phosphoramidates. The invention will permit the widespread application of the compounds in a wide range of fields including scientific and industrial research, therapeutics, and diagnostics.

DEFINITIONS

Figure 1:
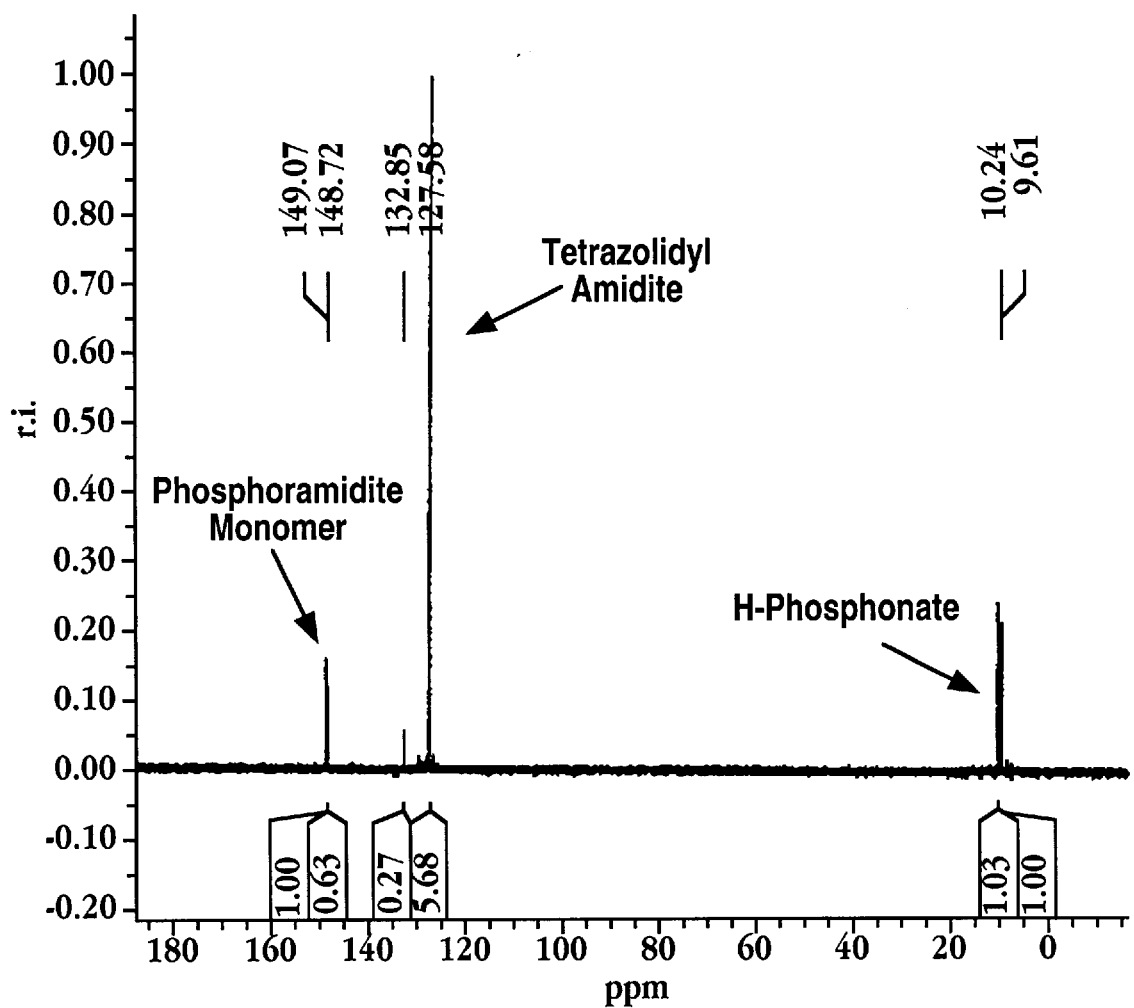
FIG. 1 is a $^{31}$P-NMR spectrum of a mixture of N6-benzoyl-3'-tritylamino-2'-deoxyadenosine-5'-(2-cyanoethyl-N,N-diisopropyl)-phosphoramidite and tetrazole.

Whenever an oligonucleotide is represented by a sequence of letters, such as "ATGUCCTG," it will be understood that the nucleotides are in 5'→3' order from left to right and that "A" denotes deoxyadenosine, "C" denotes deoxycytidine, "G" denotes deoxyguanosine, "T" denotes thymidine, and "U" denotes deoxyuridine, unless otherwise noted.

As used herein, "N3'→P5' phosphoramidate" refers to an internucleosidic linkage of the form:

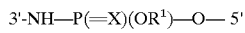

wherein the 3' and 5' refer to the carbon atoms of the sugar moieties of consecutive nucleosides which are connected by way of the linkage, and wherein $R^1$ is hydrogen or a phosphate protecting group, and X is a chalcogen, preferably oxygen or sulfur. More particularly, when $R^1$ is a phosphate protecting group it may be alkyl, alkenyl, aryl, aralkyl, or cycloalkyl containing up to 10 carbon atoms. Preferably, when $R^1$ is a phosphate protecting group it is alkyl having from 1 to 6 carbon atoms; electron-withdrawing β-substituted ethyl, particularly β-trihalomethyl-, β-cyano-, β-sulfo-, or β-nitro- substituted ethyl; electron-withdrawing substituted phenyl, particularly halo-, sulfo-, cyano-, or nitro-, substituted phenyl; or electron-withdrawing substituted phenylethyl. More preferably, when $R^1$ is a phosphate protecting group it is methyl, β-cyanoethyl, or 4- nitrophenylethyl. Most preferably, $R^1$ is hydrogen, methyl, or β-cyanoethyl. Electron-withdrawing substituents are typically halo, cyano, nitro, sulfo, or mono-, di-, or trihalomethyl, and the like. Halogen atom substituents are usually fluoro, chloro, bromo, or iodo; and preferably, they are fluoro or chloro. "Electron-withdrawing" denotes the tendency of a substituent to attract valence electrons of the molecule of which it is a part, i.e. it is electronegative, e.g. March, Advanced Organic Chemistry, pgs. 16–18 (John Wiley, New York, 1985). Guidance for selecting a -phosphate protecting group is provided in Beaucage and Iyer, Tetrahedron 48: 2223–2311 (1992). For convenience, nucleotide phosphoramidates are sometimes indicated herein by a subscripted "np" or "pn" for N3'→P5' phosphoramidates and P3'→N5' phosphoramidates, respectively. Thus, "$U_{np}U$" is a dinucleotide in which a 3'-aminouridine and a uridine are linked by an N3'→P5' phosphoramidate linkage. Similarly, 2'-fluoro substituents are indicated by a superscripted "f". Thus, "$U^f_{np}U$" is a dinucleotide in which the 5'-most 3'-amino-2'-fluorouridine is linked to a uridine by an N3'→P5' phosphoramidate linkage. A single leading subscripted "p" indicates a 5' monophosphate, and a single trailing subscripted "n" indicates a 3'-amino group.

As used herein, the term "N3'→P5' phosphoramidite linkage" (emphasis added) refers to the phosphorus (III) intermediate of the N3'→P5' phosphoramidate linkage. In accordance with the invention, an N3'→P5' phosphoramidate linkage is formed by oxidizing an N3'→P5' phosphoramidite linkage.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, such as disclosed by Uhlmann and Peyman (cited above).

As used herein, "pyrimidine" means the pyrimidines occurring in natural nucleosides, including cytosine, thymine, and uracil, and common analogs thereof, such as those containing oxy, methyl, propynyl, methoxy, hydroxyl, amino, thio, halo, and like, substituents. The term as used herein further includes pyrimidines with common protection groups attached, such as $N^4$-benzoylcytosine. Further common pyrimidine protection groups are disclosed by Beaucage and Iyer (cited above).

As used herein, "purine" means the purines occurring in natural nucleosides, including adenine, guanine, and hypoxanthine, and common analogs thereof, such as those containing oxy, methyl, propynyl, methoxy, hydroxyl, amino, thio, halo, and like, substituents. The term as used herein further includes purines with common protection groups attached, such as $N^2$-benzoylguanine, $N^2$-isobutyrylguanine, $N^6$-benzoyladenine, and the like. Further common purine protection groups are disclosed by Beaucage and Iyer (cited above).

As used herein, the term "-protected-" as a component of a chemical name refers to art-recognized protection groups for a particular moiety of a compound, e.g. "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like. Art-recognized protection groups are described in the following references: Gait, editor, Oligonucleotide Synthesis: A Practical Approach (IRL Press, Oxford, 1984); Amarnath and Broom, Chemical Reviews, Vol. 77, pgs. 183–217 (1977); Pon et al, Biotechniques, Vol. 6, pgs. 768–775 (1988); Ohtsuka et al, Nucleic Acids Research, Vol. 10, pgs. 6553–6570 (1982); Eckstein, editor, Oligonucleotides and Analogues: A Practical Approach (IRL Press, Oxford, 1991), Greene and Wuts, Protective Groups in Organic Synthesis, Second Edition, (John Wiley & Sons, New York, 1991), Narang, editor, Synthesis and Applications of DNA and RNA (Academic Press, New York, 1987), Beaucage and Iyer (cited above), and like references.

As used herein, "oligonucleotide N3'→P5' phosphoramidate" means an oligomer, usually linear, of nucleoside subunits linked by at least one N3'→P5' phosphoramidate linkage. The nucleoside subunits usually comprise nucleosides or nucleoside analogs, but may also comprise more general moieties having compatible chemistry, such as abasic sugars and other hydrocarbon moieties, such as described in the following references: Newton et al, Nucleic Acids Research, 21: 1155–1162 (1993); Griffin et al, J. Am. Chem. Soc., 114: 7976–7982 (1992); Jaschke et al, Tetrahedron Letters, 34: 301–304 (1992); Ma et al, International application PCT/CA92/00423; Zon et al, International application PCT/US90/06630; Durand et al, Nucleic Acids Research, 18: 6353–6359 (1990); Salunkhe et al, J. Am. Chem. Soc., 114: 8768–8772 (1992); and the like. More preferably, the term means an oligonucleotide wherein all internucleosidic linkages are replaced by N3'→P5' phosphoramidate linkages, i.e. the term comprehends partially as well as fully "amidated" oligomers. Still more preferably, it means an oligonucleotide wherein all the internucleosidic linkages are replaced by N3'→P5' phosphoramidate linkages and wherein the nucleoside subunits are the natural nucleosides or analogs thereof. An oligonucleotide N3'→P5' phosphoramidate of the invention in which every linkage is an N3'→P5' phosphoramidate linkage ("fully amidated") may be imbedded in or attached to other oligonucleotides or polynucleotides to form a larger oligomer which is "partially amidated." For example, the fully amidated oligonucleotide N3'→P5' phosphoramidate $A_{np}A_{np}G_{np}C_{np}C_n$ is embedded in the larger oligonucleotide $GGCCAAAA_{np}A_{np}G_{np}C_{np}C_{n-p}ACTAT$ (SEQ ID NO: 1), or is attached to "TTTATC" as a larger oligonucleotide: $A_{np}A_{np}G_{np}C_{np}C_{np}TTTATC$ (SEQ ID NO: 2). Such chimeric oligonucleotides which may be employed as PCR primers, capture probes, and the like, are included within the scope of the invention.

As used herein, the term "oxidize," "oxidation," or like terms, in reference to a phosphorus-containing internucleosidic linkage means a process or treatment for converting the phosphorus atom of the linkage from a phosphorus (III) form to a phosphorus (V) form.

As used herein, the term "phosphoramidite amino group" refers to the amino group, $-NR^4R^5$, attached to the phosphorus atom of a phosphoramidite group, and the term "phosphoramidite nitrogen" refers to the nitrogen atom of the phosphoramidite amino group.

As used herein, the terms "steric hinderance," "sterically hindered," and the like, refer to the effect on chemical reactivity of "bulky" groups, e.g. Morrison and Boyd, Organic Chemistry, page 603 (Allyn and Bacon, Boston, 1978).

DETAILED DESCRIPTION OF THE INVENTION

The invention is directed to a solid phase method of synthesizing oligonucleotide N3'→P5' phosphoramidates in which coupling of phosphoramidite monomers to a free amino group of a growing chain proceeds through the exchange of the phosphoramidite amino group of the monomer with the free 3' amino group of the growing chain. Preferably, the oligonucleotide N3'→P5' phosphoramidates produced by the method of the invention are described by the formula:

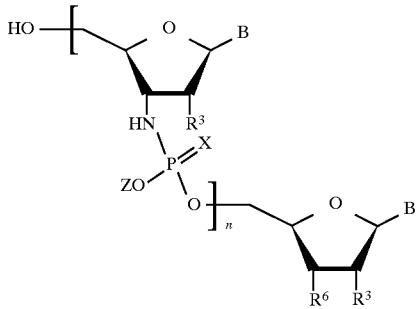

wherein: B is a purine or pyrimidine or an analog thereof; X is a chalcogen, preferably, oxygen or sulfur, and most preferably, oxygen; $R^3$ is hydrogen, fluoro, or hydroxyl, preferably, hydrogen; $R^6$ is amino or hydroxyl; and Z is hydrogen, or a cationic counter-ion such as alkali metal, amine cation such as ammonium, triethylammonium, or the like. Preferably, n is in the range of from 1 to several hundred; more preferably, n is in the range of from 1 to about 50; and most preferably, n is in the range of from 1 to 30.

Preferably, oligo-2'-fluoronucleotide N3'→P5' phosphoramidates of the invention are between 2 and 30 nucleotides in length. More preferably, they are between 8 and 25 nucleotides in length; and most preferably, they are between 8 and 20 nucleotides in length.

As mentioned above the general steps of the method include (a) providing a first nucleoside attached to a solid phase support, the first nucleoside having a protected 3' amino group; (b) deprotecting the protected 3' amino group to form a free 3' amino group; (c) reacting the free 3' amino group with a 3'-protected aminonucleoside-5'-phosphoramidite monomer to form an internucleoside N3'→P5' phosphoramidite linkage; (d) oxidizing said linkage; and (e) repeating steps (b) through (d) until the desired oligonucleotide N3'→P5' phosphoramidate is synthesized.

Even though the amine exchange reaction of the invention depends on a reversible equilibrium between reactants and products (shown below in equations 1a and 1b)—in contrast to most approaches to solid phase oligonucleotide synthesis which involve irreversible coupling steps, considerable guidance in making selections concerning coupling conditions, protecting groups, solid phase supports, linking groups, deprotection reagents, reagents to cleave products from solid phase supports, purification of product, and the like, in the context of the present invention can be found in literature, e.g. Gait, editor, (cited above); Amarnath and Broom, (cited above); Pon et al, (cited above); Ohtsuka et al, (cited above); Eckstein, editor (cited above), Greene and Wuts (cited above), Narang, editor, (cited above), Beaucage and Iyer (cited above), and like references.

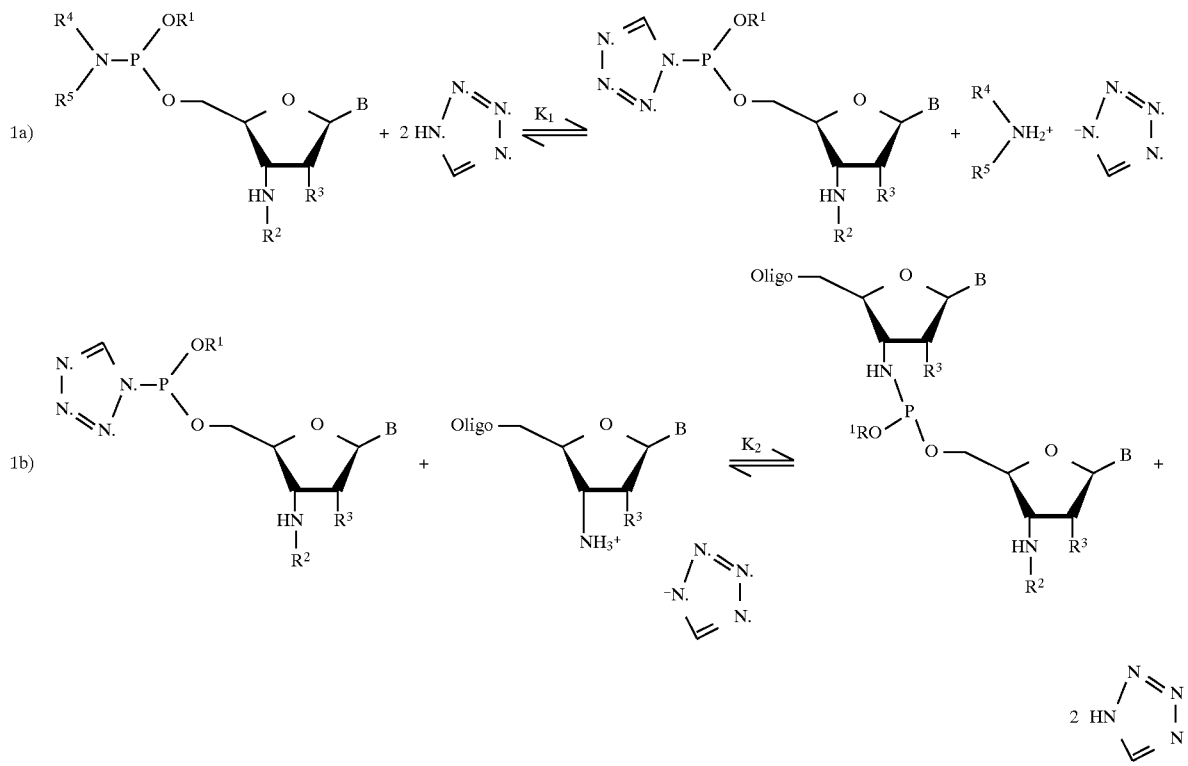

A wide variety of solid phase supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678,814; 4,413,070; and 4,046;720; and Pon, Chapter 19, in Agrawal, editor, Methods in Molecular Biology, Vol. 20, (Humana Press, Totowa, N.J., 1993). Supports further include polystyrene beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on a variety of factors, such as protection groups employed, length of final product, quantity of final product, and the like. Exemplary linking moieties are disclosed in Pon et al, Biotechniques, 6:768–775 (1988); Webb, U.S. Pat. No. 4,659,774; Barany et al, International patent application PCT/US91/06103; Brown et al, J. Chem. Soc. Commun., 1989: 891–893; Damha et al, Nucleic Acids Research, 18: 3813–3821 (1990); Beattie et al, Clinical Chemistry, 39: 719–722 (1993); Maskos and Southern, Nucleic Acids Research, 20: 1679–1684 (1992); and the like.

Preferred solid supports for use in the invention are CPG and polystyrene grafted with polyethylene glycol and possessing a terminal amino group (e.g., TentaGel-NH$_2$™, Rapp Polymere, Tubingen Germany). The aminopropyl group is a preferred spacer between CPG and the nucleoside linkage. The preferred linkage to the 5'-hydroxyl of the first nucleoside is a succinyl group which provides a base-labile ester linkage that is typically cleaved after synthesis with aqueous ammonia.

Monomers of the invention include 2'-fluoro-3'-protected aminonucleoside-5'-phosphoramidites, 2'-deoxy-3'-protected aminonucleoside-5'-phosphoramidites, 2'-protected-3'-protected aminoribonucleoside-5'-phosphoramidites, and their 3'-protected-3'-hydroxyl counterparts. Preferably, monomers of the invention are defined by the formula:

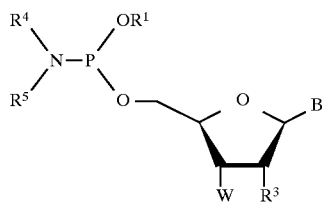

wherein B, W, $R^1$, $R^3$, $R^4$, and $R^5$ are as defined above.

More preferably, —NR$^4$R$^5$ is a sterically hindered amino group which may consist of the following preferred alternatives: First, $R^4$ and $R^5$ taken separately are alkyl, aralkyl, cycloalkyl, or cycloalkylalkyl, wherein $R^4$ and $R^5$ have a combined total of from 6 to 20 carbon atoms. Still more preferably, $R^4$ and $R^5$ taken separately are alkyl having from 1 to 8 carbon atoms. In further preference, $R^4$ and $R^5$ when taken separately are isopropyl, sec-butyl, isobutyl, t-butyl, cyclohexyl, or 2-ethylhexyl. Most preferably, when taken separately $R^4$ is isopropyl while $R^5$ is t-butyl.

Second, $R^4$ and $R^5$ taken together may form an alkylene chain containing up to 12 carbon atoms in the principal chain and a total of from 4 to 20 carbon atoms with both terminal valence bonds of said chain being attached to the nitrogen atom to which $R^4$ and $R^5$ are attached. In further preference, $R^4$ and $R^5$ taken together form an alkylene chain containing up to 6 carbon atoms in the principal chain and a total of from 4 to 12 carbon atoms with both terminal valence bonds of said chain being attached to the nitrogen atom to which $R^4$ and $R^5$ are attached.

Third, $R^4$ and $R^5$ taken together and with the nitrogen to which they are attached form a saturated nitrogen heterocycle having up to 10 carbon atoms or heteroatoms in the principal chain and a total of from 4 to 20 carbon atoms or heteroatoms altogether, such that $R^4$ and $R^5$ taken together and with the nitrogen to which they are attached contain up to three heteroatoms selected form the group consisting of nitrogen, oxygen, and sulfur. In further preference, $R^4$ and $R^5$ taken together and with the nitrogen to which they are attached form a saturated nitrogen heterocycle having up to 10 carbon atoms and up to three additional heteroatoms selected form the group consisting of nitrogen, oxygen, and sulfur. Still more preferably, $R^4$ and $R^5$ taken together and with the nitrogen to which they are attached are pyrrolidino, morpholino, tetramethylguanidinyl or piperidino. Still more preferably, $R^4$ and $R^5$ taken together and with the nitrogen to which they are attached are dimethylpiperidinyl, pyrrolidinyl, dimethylmorpholino, tetramethylmorpholino, dimethylpyrrolidinyl, tetramethylpyrrolidinyl, or tetramethylpiperidinyl. Still more preferably, $R^4$ and $R^5$ taken together and with the nitrogen to which they are attached are 2,2,6,6-tetramethylpiperidinyl, 2,6-dimethylpiperidinyl, or 2,5-dimethylpyrrolidinyl. Most preferably, $R^4$ and $R^5$ taken together and with the nitrogen to which they are attached is 2,2,6,6-tetramethylpiperidinyl.

Preferably, monomers for use in the method are 2'-deoxy-3'-protected -aminonucleoside-5'-phosphoramidites. In further preference, the phosphoramidite amino group has a pKa of at least 10.0. Still more preferably, the phosphoramidite amino group is selected such that the tetrazole activation equilibrium constant $K_1$, as defined below, and as measured in Example 9, is greater than $10\ M^{-1}$. Still more preferably, the equilibrium constant is greater than $100\ M^{-1}$; and most preferably, the equilibrium constant is greater than $1000\ M^{-1}$.

The tetrazole activation equilibrium constant $K_1$ is defined as follows:

$$K_1 = [\text{Tetrazolidyl amidite}] \frac{[R_2NH_2^+\ \text{tetrazolide}^-]}{[\text{Tetrazole}]^2\ [\text{monomer amidite}]}$$

where [Tetrazolidyl amidite] is the equilibrium concentration of the tetrazolidyl amidite intermediate, [Tetrazole] is the equilibrium concentration of tetrazole, [monomer amidite] is the equilibrium concentration of the phosphoramidite monomer, and $[R_2NH_2^+\ \text{tetrazolide}^-]$ is the equilibrium concentration of the tetrazolide salt of the amino leaving group of the phosphoramidite monomer.

Preferably, the 3'-amino protecting group of the monomer, $R^2$, is an acid-labile group, such as triphenylmethyl (i.e., trityl), p-anisyldiphenylmethyl (i.e., monomethoxytrityl or MMT), di-p-anisylphenylmethyl (i.e., dimethoxytrityl or DMT), or acid-labile urethane. Most preferably, the 3'-amino protecting group is triphenylmethyl. These protecting groups are removed by treatment with acidic solutions, most preferably with a solution of 3% dichloroacetic acid in methylene chloride. Likewise, the 3'-hydroxyl protecting group of the monomer, $R^7$, is an acid-labile group, such as trityl, MMT, DMT, or urethane. Most preferably, the 3'-hydroxyl protecting group is DMT.

As used herein, the term "free amino group" in reference to the monomers of the invention means an amino group available for reacting with the phosphoramidite group of an incoming monomer. Preferably, a free amino group is a primary amine. After the detritylation step, the amino group will generally be in the form of its salt with the conjugate base of the acid used for detritylation. This salt optionally may be neutralized with a basic solution such as 2% triethylamine or pyridine in acetonitrile after the detritylation step.

The coupling step of the invention may be carried out in the temperature range of −20 to 200 degrees Centigrade. More preferably, the reaction is carried out at ambient temperature (about 15–30 degrees Centigrade). The reaction is performed by adding a solution of the phosphoramidite monomer and a solution of an activator (or a solution containing the phosphoramidite monomer and the activator) to the reaction vessel containing the free amino group of an (oligo)nucleotide covalently attached to a solid support. Generally, activators of the invention are nucleophilic catalysts that displace the more stable phosphoramidite amino group to form a highly reactive (and much less stable) intermediate which, in turn, reacts with the free 3' amino group of a solid supported oligonucleotide N3'→P5' phosphoramidate. The mixture is then mixed by such methods as mechanically vortexing, sparging with an inert gas, etc. Alternately, the solution(s) of monomer and activator can be made to flow through a reaction vessel (or column) containing the solid supported (oligo)nucleotide with a free 3'-amino group. The monomer and the activator either can be premixed, mixed in the valve-block of a suitable synthesizer, mixed in a pre-activation vessel and pre-equilibrated if desired, or they can be added separately to the reaction vessel.

Examples of activators for use in the invention are tetrazole, 5-(ethylthio)tetrazole, 5-(4-nitrophenyl)tetrazole, 5-(2-thiophene) tetrazole, triazole, pyridinium chloride, and the like, e.g. Beaucage and Iyer (cited above); Berner et al, Nucleic Acids Research, 17: 853–864 (1989); Benson, Chem. Rev. 41: 1–61 (1947). As used herein, the term "tetrazole activator" refers to activators which are tetrazole or derivatives of tetrazole. The most preferred activator is tetrazole. Suitable solvents are acetonitrile, tetrahydrofuran, methylene chloride, and the like. Acetonitrile is preferred. A great amount of care should be exercised to use very dry (free from water) monomer, activator, and solvent for the coupling step and for the solvent used to wash the solid support immediately before the coupling step.

The choice of monomer (particularly the choice of the phosphoramidite amino group) depends on the application. Generally, for research-scale (0.01–10 μmol) phosphoramidate oligonucleotide synthesis using commercially available DNA synthesizers such as the ABI Model 394 it is useful to use a monomer which is relatively stable and relatively less reactive (as defined by the equilibrium constant $K_1$, vide supra) so the solution can be left on the instrument for multiple syntheses over a period of weeks. Another reason favoring the use of a relatively less reactive monomer for this application is the fact that instruments of this type are typically not designed to minimize the volume of reagent used. In fact, since research-scale synthesizers typically operate to some extent by flowing monomer solution through the reaction vessel (column), some of the soluble products are removed from the column (and therefore from the equilibrium), thus helping to drive the equilibrium towards completion. Also, the cost of the monomer used at this scale may be relatively less important than other factors (such as labor cost, convenience, etc). Generally, when less reactive monomers (such as diisopropylaminophosphoramidites) are used, one needs to use relatively large excesses of monomer (10–50) compared to the free amino group and one needs to use large excesses of activator to achieve reasonable reaction rates and conversions (yield).

To minimize the amount (number of equivalents) of monomer required to effect a desired coupling yield, especially when using a relatively less reactive monomer and performing a small-scale synthesis as outlined above, it is very useful to perform the couple and oxidation steps twice, using a lower concentration (and less equivalents) of monomer in each of the two coupling steps. This is because the coupling reaction is a reversible equilibration (illustrated in equations 1a and 1b). Using this method the first coupling of the cycle is performed using fairly low amounts of monomer and the equilibrium concentration of desired phosphoramidite linkage which forms under these conditions is then "locked-in" as the phosphoramadate by performing the first oxidation step of the cycle. A second coupling step is then performed, again with relatively low amounts of monomer, followed by a second oxidation step. Less monomer overall is required to achieve a desired yield using this method than if all the monomer is used in a single coupling.

The economics of large-scale production require that the amount (number of equivalents) of monomer used be minimized. In this application the cost of monomer generally becomes a larger percentage of the overall cost since the labor and some other costs do not increase linearly with the scale of the synthesis. Also, large-scale oligonucleotide synthesizers generally operate in a batch-mode rather than the flow-through mode commonly found in research-scale synthesizers, such that the technique of driving the reaction towards completion by removing soluble products from the vessel is not practical. In this application it is necessary to select a monomer which is relatively more reactive (as defined by $K_1$, vide supra). Such monomers generally possess phosphoramidite amino groups which are relatively more basic and/or more sterically hindered. The use of such reactive monomers allows the use of lower concentrations of activator to achieve reasonable reaction rates. These lower concentrations of activator help to prevent the reverse reaction of the desired product with activator to form activated intermediate (equation 1b). For these reasons significantly lower amounts of monomer (1–5 equivalents) are required.

An H-phosphoramidite impurity derived from hydrolysis of the phosphitylating agent used in the synthesis of monomers is often present in varying amounts in phosphoramidite preparations. This impurity, the concentration of which can be measured by $^{31}$P-NMR, can significantly reduce yields. Although not generally believed to be the case for conventional phosphodiester synthesis, it is very important to minimize the concentration of this impurity in monomer preparations used in the method of this invention. The use of very dry reagents and solvents during the synthesis of the monomers is very helpful to effect this end. This allows the use of less phosphitylating agent in the monomer syntheses and the generation of less of the impurity. Depending on the situation, the impurity can be further reduced by such methods as precipitation, extraction, or chromatography. It is preferable to use monomers with less than 10 mole % of this impurity. It is still more preferable to use monomers with less than 1 mole % of this impurity.

After the coupling step the resulting phosphoramidite linkage is oxidized (sulfurized) to form a stable protected phosphoramidate (phosphorothioamidate) linkage. The oxidation step can be performed immediately after the coupling solution is drained from the reaction vessel, or with a solvent wash in between. Since the phosphoramidite linkage could hydrolyze in the presence of tetrazole, the wash solution is preferably very dry and/or basic. If a wash step is not used, the oxidizing solution is preferably basic and/or very dry, or an oxidizing agent is selected that is sufficiently reactive to compete favorably with hydrolysis.

Oxidizing agents which are useful in the method of this invention include iodine, chlorine, bromine, peracids such as m-chlorobenzoic acid, hydroperoxides such as t-butylhydroperoxide, ethyl hydroperoxide, methyl hydroperoxide and the like, ozone, mixed acyl-sulfinic anhydrides such as 3H-2,1-benzoxathiolan-3-one-1-oxide, salts of persulfates such as sodium, ammonium, and tetrabutylammonium persulfate and the like, monoperoxysulfates such as oxone™, sodium and/or other hypochlorites, peroxides such as diethyl peroxide or bis(trimethylsilyl)peroxide, or hydrogen peroxide or non aqueous hydrogen peroxide equivalents such as urea/hydrogen peroxide complex, etc. Other useful oxidizing agents which may be used to convert phosphorus (III) to phosphorus (V) are described in Beaucage and Iyer (cited above). Sulfurizing agents for use in the invention include elemental sulfur, thiuram disulfides such as tetraethyl thiuram disulfide, acyl disulfides such as phenacyldisulfide, phosphinothioyl disulfides such as S-Tetra™, and 1,1-dioxo-3H-1,2-benzodithiol-3-one.

Many of the oxidizing and sulfurizing agents listed have a tendency to undergo an undesired Arbuzov side reaction in parallel with the desired oxidation (Beaucage and Iyer, cited above). This Arbuzov side reaction is diagrammed below with the conventional oxidizing agent, iodine/water/lutidine/THF, most often used in phosphodiester synthesis:

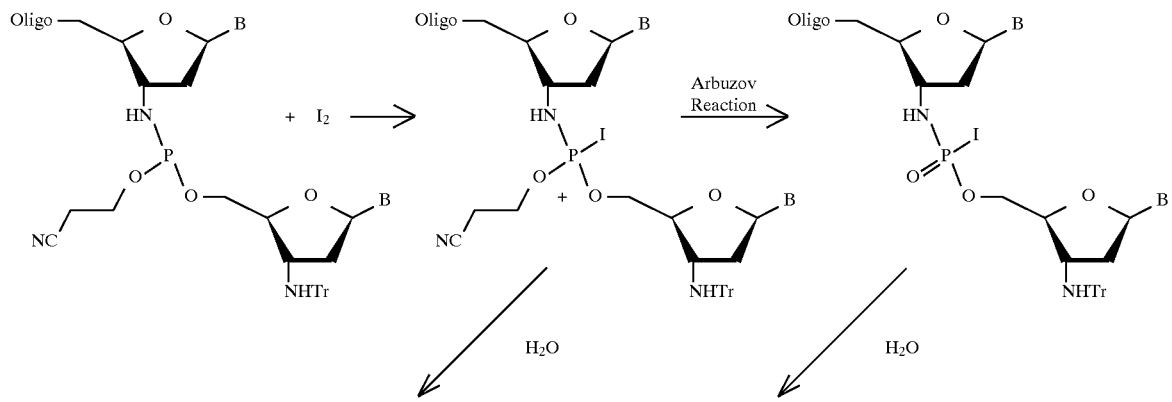

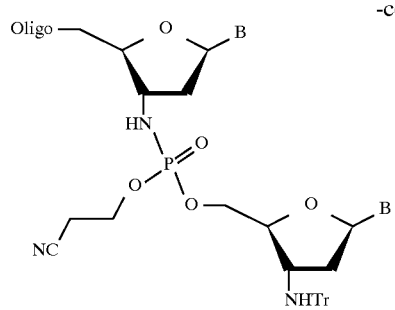

Desired Product

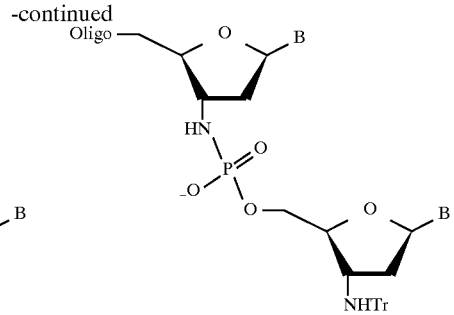

Deprotected Product

The Arbuzov side reaction is not very harmful in normal diester synthesis, but it is very harmful in phosphoramidate synthesis because the resulting deprotected phosphoramidate is unstable to the acidic conditions of subsequent detritylation steps, and oligonucleotide fragmentation results. Hydrogen peroxide is a preferred oxidizing agent for use in this invention. A preferred embodiment is to use a solution of 1.5% hydrogen peroxide, 3.5% water, 20% pyridine, and 75% THF.

In one embodiment of the invention the unreacted 3'-amino groups remaining after the (last) oxidation step of a cycle may be capped with a suitable capping agent before the next detritylation step to render them inert to subsequent coupling steps. This capping step not only improves the HPLC profile to make purification more facile, but also significantly improves the overall yield of product, perhaps by eliminating the unreacted 3' amino groups from competing in the equilibrium. Capping reagents useful in the method of this invention include electrophilic reagents such as such as acetic anhydride and isobutyric anhydride, acid chlorides such as adamantyl carbonyl chloride, pivaoyl chloride, and the like, isothiocyanates, chloroformates, etc. Also useful are phosphoramidites in conjunction with an activator and followed by oxidation, and H-phosphonate salts such as triethylammonium isopropyl-H-phosphonate used in conjunction with an acid chloride such as pivaloyl chloride or adamantyl carbonyl chloride.

The 3'-amino protecting groups in the monomer, e.g. trityl, make the amino group less reactive with the phosphoramidite group of the monomers and with capping agents. However, this protection is not as complete as is the case with the similarly protected 5'-hydroxyl group of conventional phosphodiester synthesis. For this reason a slightly less reactive capping agent such as isobutyric anhydride is preferred over the acetic anhydride most often used in phosphodiester synthesis. Either the isobutyric anhydride or acetic anhydride can be used as a 1:1:8 anhydride:lutidine::tetrahydrofuran (by volume) solution and used in equal parts with a solution of 1-methylimidizole in tetrahydrofuran as supplied by PE Applied Biosystems (Foster City, Calif.).

The oligonucleotide is cleaved from the solid support and deprotected after completion of the chain assembly using aqueous ammonia or other means as described in references cited above. The oligonucleotide may be cleaved from the support with its terminal amino-protecting group (or hydroxyl protecting group in some cases) intact. This is desirable in some situations in which the trityl or other protecting group is used as an aid in purification, such as by reverse phase or ion-exchange HPLC. However, when trityl protecting groups are used and are removed with acid treatment after cleavage from the support, deprotection, and purification there is a strong tendency for the deprotected phosphoramidate linkages to undergo undesired fragmentation, therefore great care is required during this step.

Alternately, the terminal amino protecting group (such as trityl) may be removed with acid before cleavage from the support. In this case the phosphoramidate linkages are still protected and fragmentation is avoided. The oligonucleotide is then cleaved from the support and deprotected as above. The phosphoramidate oligonucleotide may be purified by ion-exchange HPLC, reversed-phase HPLC, or other means.

EXAMPLE 1

Preparation of 2'-Deoxy-3'-tritylaminothymidine-5'-phosphoramidite Monomers

The synthesis of 3'-(Trityl)amino-3'-deoxythymidine-5'-(2-cyanoethyl N,N-diisopropyl) phosphoramidite, 4t is outlined in Scheme I. 3'-Azido-5'-O-(4-methoxybenzoyl)-3'-deoxythymidine, it, was synthesized by the method of Czernecki and Valery, Synthesis, 1991: 239.

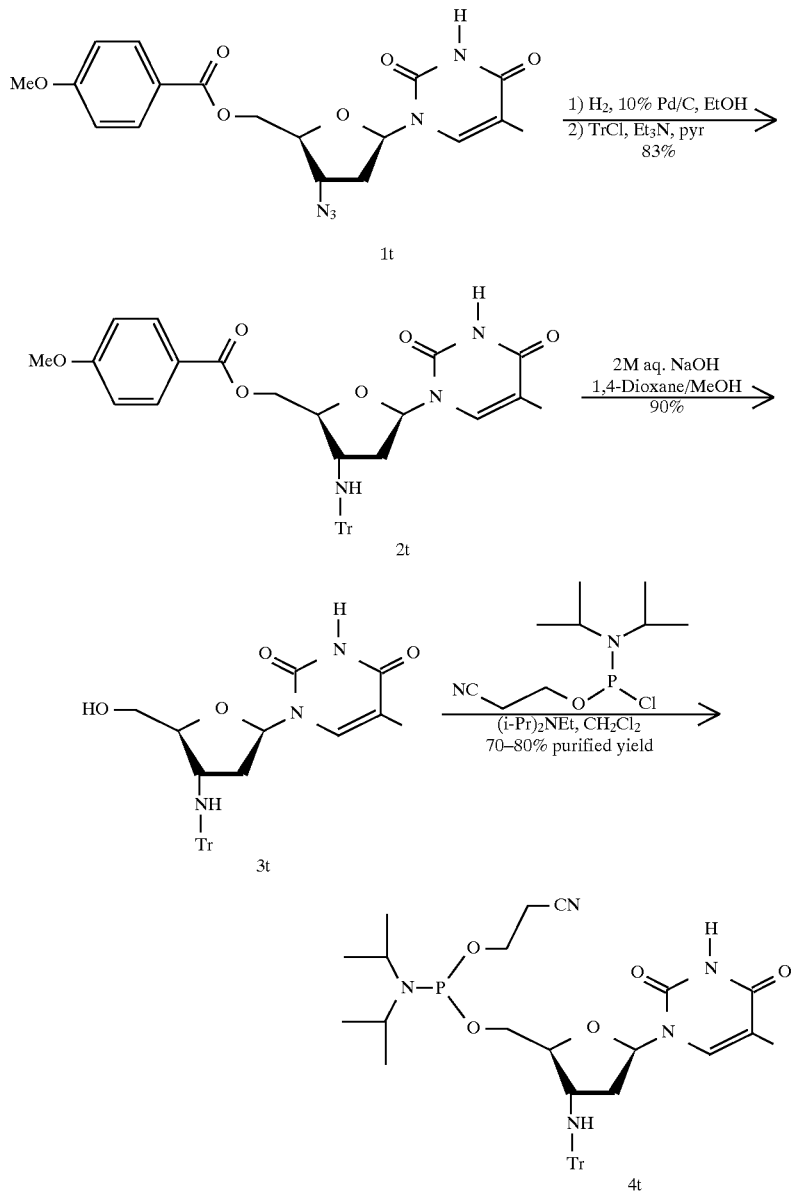

Scheme I

3'-(Trityl)amino-5'-(4-methoxybenzoyl)-3'-deoxythymidine, 2t. 3'-Azido-5'-O-(4-methoxybenzoyl)-3'-deoxythymidine, 1t (10.0 g, 24.9 mmol), was dissolved in ethanol (500 mL) and reduced via hydrogenation (60 psi $H_2$) in the presence of 10% Pd/C (1.0 g) for 16 h. Subsequent removal of the catalyst via filtration and evaporation of solvent in vacuo, afforded 92% yield (8.6 g, 22.9 mmol) of the corresponding 3'-amine which was taken on directly to the next reaction. The 5'-(4-methoxybenzoyl)-3'-amino-3'deoxythymidine (8.6 g, 22.9 mmol) was azeotroped from pyridine (2×50 mL), and dissolved in anhydrous pyridine (50 mL). To this solution was added triethylamine (6.71 mL, 48.1 mmol) and trityl chloride (7.0 g, 25.2 mmol). This mixture was stirred for 2 h at ambient temperature, an additional portion of trityl chloride was added (1.9 g, 6.9 mmol), and the reaction was stirred an additional 2 h. Solvents were removed in vacuo, and the crude product was purified on silica (2–5% MeOH/$CH_2Cl_2$) to afford 90% yield (12.7 g, 20.6 mmol) of 3'-(Trityl)amino-5'-(4-methoxybenzoyl)-3'-deoxythymidine, 2t.

3'-(Trityl)amino-3'-deoxythymidine, 3t. The 5'-O-anisoyl protecting group was removed by dissolving 2t (30.1 g, 48.7 mmol) in 57:43 1,4-dioxane/MeOH (150 mL), followed by the addition of 2M aq. NaOH (73.1 mL, 146.2 mmol). After stirring for 1.5 h at ambient temperature, the reaction mixture was neutralized with Dowex 50W-X8 cation exchange resin (ca. 150 g of dry pyridinium $H^+$-form, 1.6 meq/g). Once the pH was neutral (ca. 10 min), the resin was filtered, washed extensively with $CH_2Cl_2$ and MeOH, and the crude product was concentrated in vacuo. The residue was redissolved in EtOAc (500 mL) and extracted with saturated. aq. $NaHCO_3$ (2×250 mL), $H_2O$ (250 mL), and saturated. aq. NaCl (250 mL). After drying over $Na_2SO_4$ and filtration, the solvents were removed in vacuo, and the resulting foam was redissolved in 95:5 CH$_2$Cl$_2$/MeOH (300 mL). This solution was added slowly to a rapidly stirring mixture of 1:1 Et$_2$O/hexane (1250 mL) to precipitate the pure 3'-(Trityl)amino-3'-deoxythymidine, 3t, in 90% yield (21.2 g, 43.8 mmol). Conversion to phosphoramidite monomers and/or succinylated nucleoside is described in Examples 5–7 below.

EXAMPLE 2

Preparation of 2'-Deoxy-3'-tritylaminocytidine-5'-phosphoramidite Monomers

The synthesis of N$^4$-Benzoyl-3'-(trityl)amino-2',3'-dideoxycytidine-5'-(2-cyanoethyl N,N-diisopropyl) phosphoramidite, 4c is outlined in Scheme II.

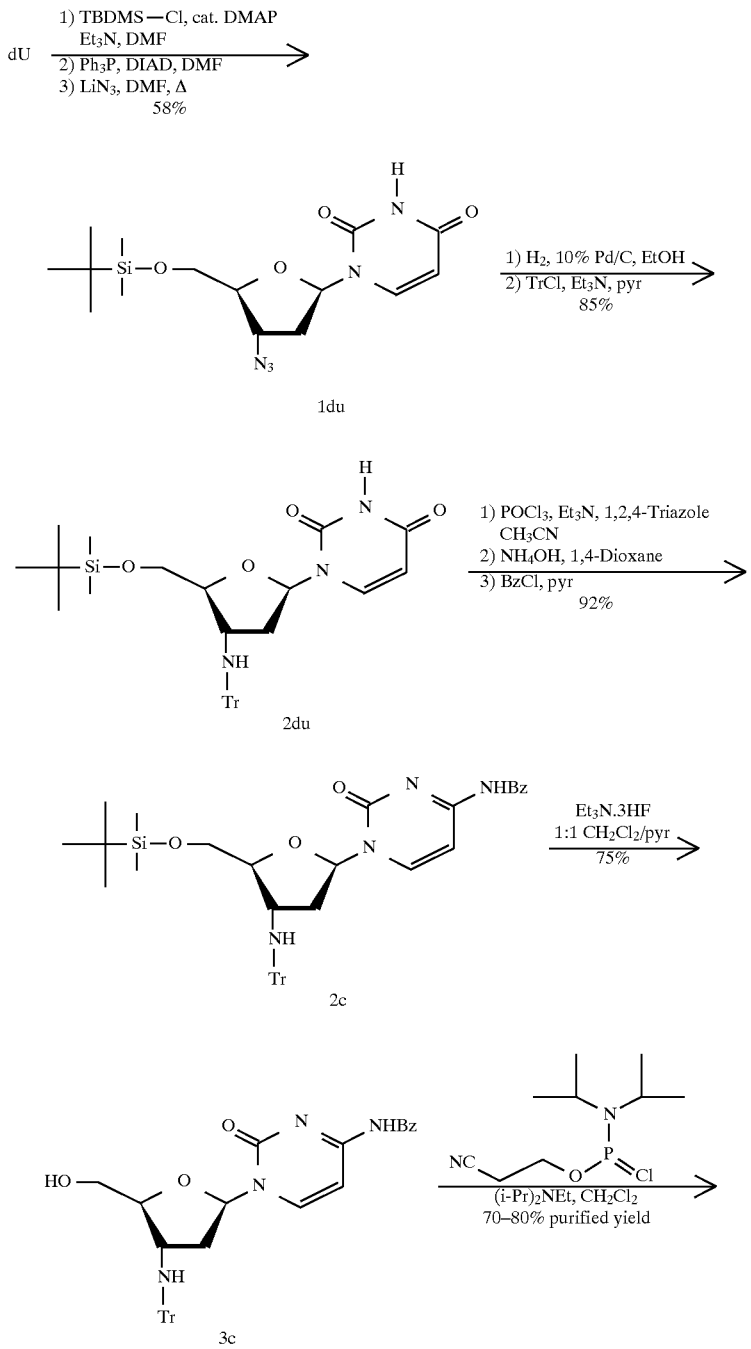

-continued
Scheme II

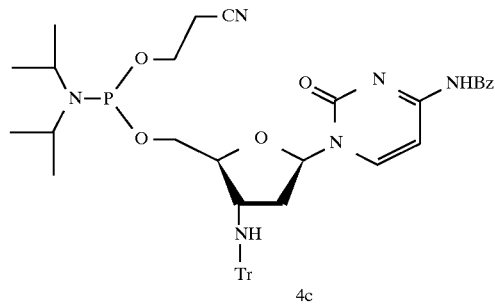

4c

3'-azido-5'-O-(tert-butyldimethylsilyl)-2',3'-dideoxyuridine, 1du. 2'-Deoxyuridine (11.4 g, 50 mmol) was thoroughly dried by coevaporating in vacuo with anhydrous DMF (2×100 mL). DMF (100 mL) was then added, followed by triethylamine (8.36 mL, 60 mmol), 4-dimethylaminopyridine (0.31 g, 2.5 mmol), and tert-butyldimethylsilyl chloride (8.29 g, 55.0 mmol). The reaction mixture was stirred for 1 h at RT, diluted with dichloromethane (600 mL) and extracted with $H_2O$ (3×200 mL), and saturated aq. NaCl (200 mL). The organic layer was dried over $Na_2SO_4$, filtered and concentrated in vacuo. The resulting residue was purified on silica (2–10% MeOH/$CH_2Cl_2$) to afford 80% yield (13.7 g, 40.0 mmol) of 5'-O-(tert-butyldimethylsilyl)-2'-deoxyuridine. Triphenylphosphine (16.8 g, 64.0 mmol) and DMF (100 mL) were added, and to this stirring mixture was added a solution of diisopropylazodicarboxylate (12.6 mL, 64.0 mmol) in DMF (20 mL). After stirring 2 h at RT, the reaction mixture was concentrated in vacuo to ca. 30 mL, and poured into $Et_2O$ (1200 mL). The desired 2,3'-anhydro-5'-O-(tert-butyldimethylsilyl)-2'-deoxyuridine began precipitating out after 10 min of rapid stirring. The resulting mixture was placed in the refrigerator overnight, the precipitate was collected by filtration, washed with additional cold $Et_2O$ (2×300 mL), and dried in vacuo to afford 90% yield (11.7 g, 36.0 mmol) of 2,3'-anhydro-5'-O-(tert-butyldimethylsilyl)-2'-deoxyuridine as a white solid, which was not purified further. The 2,3'-anhydro-5'-O-(tert-butyldimethylsilyl)-2'-deoxyuridine (33.8 g, 104.2 mmol) was then reacted with $LiN_3$ (7.65 g, 156.3 mmol) in DMF (300 mL) at 95°–100° C. for 48 h. The resulting brown, homogeneous mixture was then cooled to RT, concentrated in vacuo to an oil, dissolved in EtOAc (800 mL), and extracted with $H_2O$ (200 mL). The aqueous layer was extracted twice more with EtOAc (75 mL), and the combined organics were washed with $H_2O$ (3×250 mL) and once with saturated. aq. NaCl (250 mL). The EtOAc solution was dried over $Na_2SO_4$, filtered, and concentrated in vacuo, to afford 87% yield (33.2 g, 90.3 mmol) of 3'-azido-5'-O-(tert-butyldimethylsilyl)-2',3'-dideoxyuridine, 1du, as a brownish foam, which was taken on directly to hydrogenation.

3'-(Trityl)amino-5'-O-(tert-butyldimethylsilyl)-2',3'-dideoxyuridine, 2du. Crude 1du (33.2 g, 90.3 mmol) was dissolved in 2:1 EtOH/$CH_2Cl_2$ (300 mL) and reduced via hydrogenation (60 psi $H_2$) in the presence of 10% Pd/C (3.0 g) for 18 h. Subsequent removal of the catalyst via filtration and evaporation of solvent in vacuo, afforded quantitative yield (30.4 g, 89.8 mmol) of the corresponding 3'-amine which was taken on directly to the next reaction. The 5'-O-(tert-butyldimethylsilyl)-3'-amino-2',3'-dideoxyuridine (30.4 g, 89.8 mmol) was azeotroped from pyridine (2×300 mL), and dissolved in a mixture of $CH_2Cl_2$ (600 mL) and anhydrous pyridine (70 mL). To this solution was added triethylamine (25.0 mL, 179.6 mmol) and trityl chloride (35.0 g, 125.7 mmol), and the reaction mixture was stirred for 2 h at ambient temperature. Solvents were removed in vacuo, and the crude product was purified on silica (1–5% MeOH/$CH_2Cl_2$) to afford 85% yield (44.3 g, 75.9 mmol) of 3'-(Trityl)amino-5'-O-(tert-butyldimethylsilyl)-2',3'-dideoxyuridine, 2du.

$N^4$-Benzoyl-3'-(trityl)amino-5'-O-(tert-butyldimethylsilyl)-2',3'-dideoxycytidine, 2c. Triethylamine (22.5 mL, 161.1 mmol) was added dropwise over a period of 10 min to a stirring mixture of 1,2,4-triazole (11.1 g, 161.1 mmol) and phosphorus oxychloride (3.5 mL, 37.1 mmol) in anhydrous acetonitrile (125 mL) at 0° C. To this cold, stirring mixture was added 2du (9.4 g, 16.1 mmol) as a solution in acetonitrile (50 mL). This mixture was stirred at RT for 2 h, triethylamine (30 mL) and $H_2O$ (10 mL) were added to quench the reaction and promote dissolution, and solvents were removed in vacuo. The resulting brown solid was redissolved in $CH_2Cl_2$ (250 mL), extracted with saturated. aq. $NaHCO_3$ (3×150 mL), saturated. aq. NaCl, dried over $Na_2SO_4$, filtered, and concentrated in vacuo to afford quantitative yield (10.2 g, 16.1 mmol) of 3'-(Trityl)amino-5'-O-(tert-butyldimethylsilyl)-2',3'-dideoxy-4-(1,2,4-triazol-1-yl)uridine as an orangish solid. This crude material was dissolved in 1,4-dioxane (200 mL) and cold, concentrated $NH_4OH$ (50 mL) was added. The reaction mixture was stirred at RT for 4 h, and concentrated in vacuo to afford quantitative yield (9.4 g, 16.1 mmol) of 3'-(Trityl)amino-5'-O-(tert-butyldimethylsilyl)-2',3'-dideoxycytidine as a beige solid. This crude material was then azeotroped from anhydrous pyridine (2×200 mL), redissolved in pyridine (200 mL), and to this stirring solution was added benzoyl chloride (2.2 mL, 19.3 mmol) at 0° C. The reaction was then stirred at RT for 16 h, externally cooled to 0° C., quenched with $H_2O$ (40 mL), and after stirring 5 min, conc. aq. ammonia (40 mL) was added and the reaction mixture was stirred for an additional 15 min at 0° C. Solvents were removed in vacuo, the residue was redissolved in $CH_2Cl_2$ (125 mL), and extracted with saturated. aq. $NaHCO_3$ (3×75 mL), dried over $Na_2SO_4$, filtered and concentrated in vacuo. This crude material was purified on silica (1–5% MeOH $CH_2Cl_2$) to afford 92% yield (10.2 g, 14.8 mmol) of $N^4$-Benzoyl-3'-(trityl)amino-5'-O-(tert-butyldimethylsilyl)-2',3'-dideoxycytidine, 2c.

$N^4$-Benzoyl-3'-(trityl)amino-2',3'-dideoxycytidine, 3c. The 5'-TBDMS protecting group was removed by dissolving 2c (5.8 g, 8.5 mmol) in 1:1 $CH_2Cl_2$/pyridine (25 mL) and reacting with Et₃N.3HF (6.9 mL, 42.6 mmol) for 16 h. The reaction mixture was diluted with CH₂Cl₂ (200 mL) and extracted with H₂O (2×50 mL), and saturated. aq. NaCl (50 mL). The organic layer was dried over Na₂SO₄, filtered, and the solvent was removed in vacuo. The crude product was purified on silica (3% MeOH/CH₂Cl₂) to afford 75% yield (3.7 g, 6.4 mmol) of N⁴-Benzoyl-3'-(trityl)amino-2',3'-dideoxycytidine, 3c. Conversion to phosphoramidite monomers and/or succinylated nucleoside is described in Examples 5–7 below.

EXAMPLE 3

Preparation of 2'-Deoxy-3'-tritylaminoguanosine-5'-phosphoramidite Monomers

The synthesis of N²-Isobutyryl-3'-(trityl)amino-2',3'-dideoxyguanosine-5'-(2-cyanoethyl N,N-diisopropyl) phosphoramidite, 4g is outlined in Scheme III. 5'-O-Benzoyl-N²-isobutyryl-2'-deoxyguanosine and 3'-O-Benzoyl-N²-isobutyryl-2'-deoxyxyloguanosine were prepared as described previously, Reese et al, J. Chem. Soc. Perkin Trans. I, 1984: 1263.

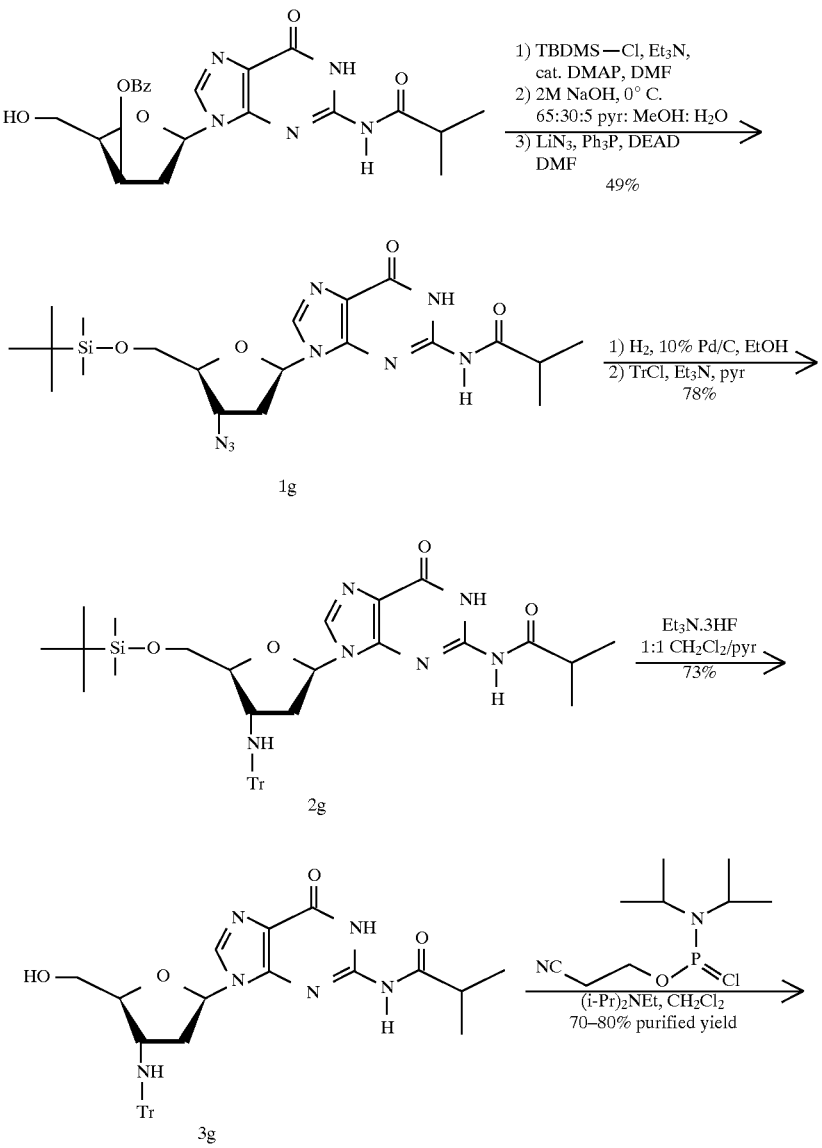

-continued
Scheme III

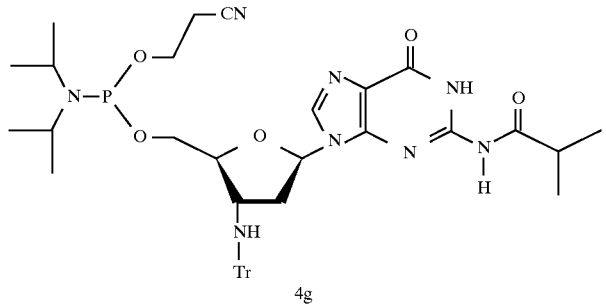

4g

5'-O-(tert-Butyldimethylsilyl)-N²-isobutyryl-3'-azido-2',3'-dideoxyguanosine, 1 g. To a stirring solution of 3'-O-Benzoyl-N²-isobutyryl-2'-deoxyxyloguanosine (4.86 g, 11.0 mmol) in DMF (20 mL), was added triethylamine (3.4 mL, 24.2 mmol), 4-dimethylaminopyridine (54 mg, 0.44 mmol), and tert-butyldimethylsilyl chloride (3.31 g, 22.0 mmol). The reaction was stirred for 2 h at RT, methanol (10 mL) was added and after stirring an additional 5 min, the reaction mixture was concentrated in vacuo. The residue was redissolved in CH₂Cl₂ (150 mL), washed with H₂O (3×40 mL), and saturated. aq. NaCl (60 mL). The organic layer was dried over Na₂SO₄, filtered, and concentrated in vacuo to afford 6.40 g of a reddish-colored foam. To this crude material was added, a pre-chilled (ca. 5° C.) solution of 2M NaOH in 65:30:5 pyridine:MeOH:H₂O (44.0 mL, 87.9 mmol). The reaction mixture was stirred in an ice bath for 20 min and neutralized with 1M HCl (97 mL) to pH 7. The reaction mixture was concentrated in vacuo to ca. 50 mL, and extracted with CH₂Cl₂ (3×75 mL). The combined organics were washed with saturated. aq. NaCl (50 mL), dried over Na₂SO₄, filtered, and concentrated in vacuo to afford 82% yield (4.1 g, 9.1 mmol) of 5'-O-(tert-butyldimethylsilyl)-N²-isobutyryl-2'-deoxyxyloguanosine as a sandy-colored foam, which was taken on to the next reaction without further purification. To crude 5'-O-(tert-butyldimethylsilyl)-N²-isobutyryl-2'-deoxyxyloguanosine (47.3 g, 104.7 mmol), was added LiN₃ (15.4 g, 314.1 mmol), triphenylphosphine (41.2 g, 157.1 mmol), and anhydrous DMF (1000 mL). Diethylazodicarboxylate (24.7 mL, 157.1 mmol) was added and the reaction mixture was stirred for 5 h at RT under argon. H₂O (20 mL) was added and the reaction mixture was concentrated in vacuo. The residue was dissolved in EtOAc (1500 mL), washed with H₂O (3×1000 mL), saturated. aq. NaCl (1000 mL), dried over Na₂SO₄, filtered, and concentrated in vacuo. The residue was purified on silica (1–5% MeOH/CH₂Cl₂), although this afforded >100% yield (112.7 g) of impure 5'-O-(tert-Butyldimethylsilyl)-N²-isobutyryl-3'-azido-2',3'-dideoxyguanosine, 1g. This contaminated product was not purified further, and was taken on directly to hydrogenation and purified as the 3'-amine.

5'-O-(tert-Butyldimethylsilyl)-N²-isobutyryl-3'-(trityl) amino-2',3'-dideoxyguanosine, 2g. Crude compound 1g (49.9 g,, 104.7 mmol) was dissolved in (warm) ethanol (1600 mL) and hydrogenated (60 psi H₂) in the presence of 10% Pd/C (2.5 g) for 16 h at RT. The catalyst was removed via filtration, and the solvent was evaporated in vacuo to afford the crude 5'-O-(tert-butyldimethylsilyl)-N²-isobutyryl-3'-amino-2',3'-dideoxyguanosine, which was purified on silica (2–6% MeOH/CH₂Cl₂ and then 1% Et₃N/6% MeOH/CH₂Cl₂) to afford 60% yield (28.5 g, 63.2 mmol) of pure 5'-O-(tert-butyldimethylsilyl)-N²-isobutyryl-3'-amino-2',3'-dideoxyguanosine as an off-white foam. The 3'-amine (28.5 g, 63.2 mmol) was protected by reacting with triethylamine (17.6 mL, 126.4 mmol) and trityl chloride (28.2 g, 101.1 mmol) in pyridine (500 mL) for 16 h at RT. Solvents were removed in vacuo and the residue was purified on silica (1–5% MeOH/CH₂Cl₂) to afford quantitative yield (43.8 g, 63.2 mmol) of 5'-O-(tert-butyldimethylsilyl)-N²-isobutyryl-3'-(trityl)amino-2',3'-dideoxyguanosine, 2g.

N²-Isobutyryl-3'-(trityl)amino-2',3'-dideoxyguanosine, 3g. The 5'-TBDMS protecting group was removed by dissolving 2g (5.9 g, 8.5 mmol) in 1:1 CH₂Cl₂/pyridine (25 mL) and reacting with Et₃N.3HF (6.9 mL, 42.6 mmol) for 16 h. The reaction mixture was diluted with CH₂Cl₂ (200 mL) and extracted with H₂O (2×50 mL), and saturated. aq. NaCl (50 mL). The organic layer was dried over Na₂SO₄, filtered, and the solvent was removed in vacuo. The crude product was purified on silica (2–5% MeOH/CH₂Cl₂) to afford 73% yield (3.6 g, 6.2 mmol) of N²-Isobutyryl-3'-(trityl)amino-2', 3'-dideoxyguanosine, 3g. Conversion to phosphoramidite monomers and/or succinylated nucleoside is described in Examples 5–7 below.

EXAMPLE 4

Preparation of 2'-Deoxy-3'-tritylaminoadenosine-5'-phosphoramidite Monomers

The synthesis of N⁶-Benzoyl-3'-(trityl)amino-2',3'-dideoxyadenosine-5'-(2-cyanoethyl N,N-diisopropyl) phosphoramidite, 4a is outlined in Scheme IV. N⁶-Benzoyl-9-(5-O-benzoyl-2-deoxy-β-D-threo-pentofuranosyl)adenine was synthesized by the method of Herdewijn, J. Org. Chem., 53: 5050 (1988).

Scheme IV

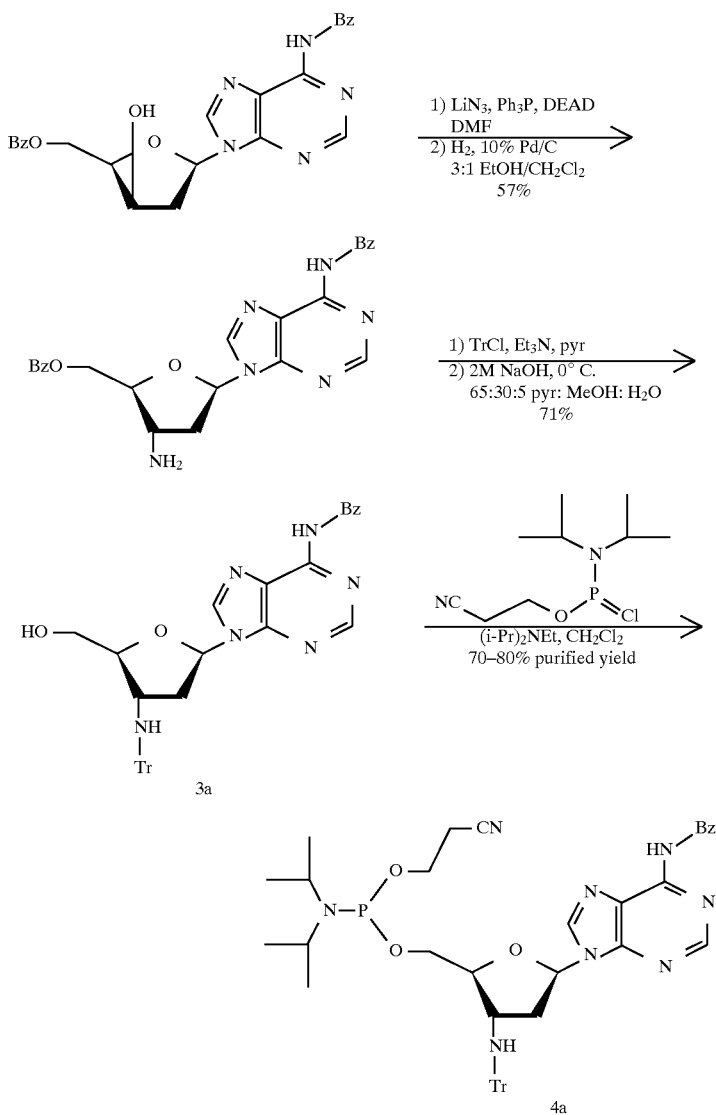

5'-O-(Benzoyl)-N⁶-benzoyl-3'-azido-2',3'-dideoxyadenosine, 1a. N⁶-Benzoyl-9-(5-O-benzoyl-2-deoxy-β-D-threo-pentofuranosyl)adenine (7.0 g, 15.3 mmol), triphenylphosphine (6.0 g, 22.9 mmol), and $LiN_3$ (2.8 g, 56.4 mmol) were dissolved in DMF (100 mL). To this stirring mixture was added diethylazodicarboxylate (3.6 mL, 22.9 mmol) in one portion, the reaction was stirred for 2.5 h at RT, and the reaction was quenched with $H_2O$ (10 mL). The solvents were removed in vacuo, the residual oil was redissolved in EtOAc (300 mL) and extracted with $H_2O$ (2×200 mL) and saturated. aq. NaCl (200 mL). The organic layer was dried over $Na_2SO_4$, filtered, and concentrated in vacuo. The resulting residual oil was purified on $SiO_2$ (2–5% MeOH/$CH_2Cl_2$) to afford 5'-O-Benzoyl-N²-benzoyl-3'-azido-2',3'-dideoxyadenosine, 1a, as an amber foam, which was taken on directly to hydrogenation.

N⁶-Benzoyl-3'-(trityl)amino-2',3'-dideoxyadenosine, 3a. Crude 1a was dissolved in 3:1 EtOH/$CH_2Cl_2$ (200 mL) and reduced via hydrogenation (60 psi $H_2$) in the presence of 10% Pd/C (0.7 g) for 18 h. Subsequent removal of the catalyst via filtration and evaporation of solvent in vacuo, afforded 57% (4.0 g, 8.7 mmol) of the corresponding 3'-amine which was taken on directly to the next reaction. 5'-O-Benzoyl-N⁶-benzoyl-3'-amino-2',3'-dideoxyadenosine (3.9 g, 8.5 mmol) was dissolved in $CH_2Cl_2$ (50 mL), triethylamine (2.9 mL, 20.8 mmol) was added, followed by the addition of trityl chloride (2.9 g, 10.2 mmol). After stirring for 1.5 h at RT the reaction mixture was diluted with $CH_2Cl_2$ (50 mL), and extracted with $H_2O$ (2×50 mL) and saturated. aq. NaCl (50 mL). The organic layer was dried over $Na_2SO_4$, filtered, and concentrated in vacuo to afford crude 5'-O-Benzoyl-N⁶-benzoyl-3'-(trityl)amino-2',3'-dideoxyadenosine, which was taken on directly to hydrolysis of the 5'-benzoyl protecting group. The crude 5'-O-Benzoyl-N⁶-benzoyl-3'-(trityl)amino-2',3'-dideoxyadenosine (ca. 6.0 g, 8.5 mmol) was dissolved in 1:1 THF/MeOH (100 mL) and cooled to 0° C. To this mixture was added pre-chilled 2M aq. NaOH (13.7 mL, 27.4 mmol), and the reaction mixture was stirred at 0° C. for 20 min. At this time the reaction appeared to be only about 50% complete, so additional 2M aq. NaOH (10.0 mL, 20 mmol) was added. After stirring an additional 15 min at 0° C., the reaction was neutralized with Dowex 50W-X8 cation exchange resin (ca. 40 g of dry pyridinium H$^+$-form, 1.6 meq/g) to pH 6. The resin was filtered and washed extensively with MeOH and THF, and solvents were removed in vacuo. The residue was redissolved in CH$_2$Cl$_2$ (300 mL) and extracted with H$_2$O (150 mL), saturated. aq. NaHCO$_3$ (2×150 mL), H$_2$O (150 mL), and saturated. aq. NaCl (150 mL). After drying over Na$_2$SO$_4$, the solution was filtered and concentrated in vacuo. The residue was purified on SiO$_2$ (2–3% MeOH/CH$_2$Cl$_2$) to afford 71% yield (3.6 g, 6.0 mmol) of N$^6$-Benzoyl-3'-(trityl)amino-2',3'-dideoxyadenosine, 3a, as a white foam. Conversion to phosphoramidite monomers and/or succinylated nucleoside is described in Examples 5–7 below.

EXAMPLE 5

Preparation of 3'-(trityl)amino-2',3'-dideoxynucleoside-5'-(2-cyanoethyl N,N-diisopropyl) phosphoramidites, 4a, 4c, 4g and 4t To 8.4 mmol 3'-(trityl)amino-2,'3'-dideoxynucleoside (3a, 3c, 3g, or 3t) (previously azeotroped 2 times from CH$_3$CN) in 25 mL of CH$_2$Cl$_2$ under argon was added 2.0 mL (11.8 mmol) of N,N-diisopropylethylamine and 2.1 mL (9.4 mmol) of 2-cyanoethyl N,N-diisopropylchlorophosphoramidite. After stirring for 15 min the reaction was diluted with CH$_2$Cl$_2$ and extracted with saturated. aq. NaHCO$_3$ and saturated. aq. NaCl. The organic layer was dried (Na$_2$SO$_4$), filtered, and concentrated in vacuo. N$^6$-Benzoyl-3'-(trityl)amino-2',3'-dideoxyadenosine-5'-(2-cyanoethyl N,N-diisopropyl) phosphoramidite, 4a, was purified on SiO$_2$ (5%Et$_3$N/2% methanol/toluene) which gave 5.82 g (87.1%) of pure phosphoramidite. $^{31}$P NMR (CD$_3$CN) δ 148.6, 149.2. N$^4$-Benzoyl-3'-(trityl)amino-2',3'-dideoxycytidine-5'-(2-cyanoethyl N,N-diisopropyl) phosphoramidite, 4c, was purified on SiO$_2$ (3% MeOH/5% Et$_3$N/toluene) and gave 5.58 g (86.0%) pure product. $^{31}$P NMR (CD$_3$CN) δ 149.3, 149.6. N$^2$-Isobutyryl-3'-(trityl)amino-2',3'-dideoxyguanosine-5'-(2-cyanoethyl N,N-diisopropyl) phosphoramidite, 4g, was precipitated under argon from 10 mL CH$_2$Cl$_2$ into rapidly stirring ethyl ether (200 mL) and hexane (200 mL) at 4° C. to remove the hydrogen phosphoramidate impurity which cannot be removed by column chromatography in this case. The solid was filtered, washed with hexane, and dried in vacuo. This precipitation step was repeated and the resulting solid was purified further on SiO$_2$ (10% Et$_3$N/CH$_2$Cl$_2$) and gave 4.51 g (69%) pure phosphoramidite product. $^{31}$P NMR (CD$_3$CN) δ 148.7, 149.4. 3'-(Trityl)amino-3'-deoxythymidine-5'-(2-cyanoethyl N,N-diisopropyl) phosphoramidite, 4t, was purified on SiO$_2$ (2% Et$_3$N/CH$_2$Cl$_2$) and afforded 4.06g (70.7%) pure phosphoramidite and some mixed fractions. $^{31}$P NMR (CD$_3$CN) δ 149.4, 149.5.

EXAMPLE 6

Preparation of 3'-(trityl)amino-2',3'-dideoxynucleoside-5'-(2-cyanoethyl-2,2,6,6-tetramethylpiperidine)phosphoramidites 5a, 5c, 5g and 5t To 8.4 mmol 3'-(trityl)amino-2,'3'-dideoxynucleoside (3a, 3c, 3g, or 3t) (previously azeotroped 2 times from CH$_3$CN) in 25 mL of CH$_2$Cl$_2$ cooled to 4° C. under argon was added 1.9 mL (12.6 mmol) of DBU and 5.2 mL (8.4 mmol) of a solution of 2-cyanoethyl 2,2,6,6-tetramethylpiperidinechlorophosphoramidite in CH$_2$Cl$_2$ (conc.=1.626 mmol/mL). The ice bath was removed and the solution was stirred for 30–60 min. To avoid decomposition, the crude reaction was loaded directly onto a SiO$_2$ column (3% MeOH/5% Et$_3$N/toluene for 5a, 5c, and 5t, and 10% Et$_3$N/CH$_2$Cl$_2$ for 5g) for purification. In all cases further purification was necessary as indicated for each product. N$^6$-Benzoyl-3'-(trityl)amino-2',3'-dideoxyadenosine-5'-(2-cyanoethyl 2,2,6,6-tetramethylpiperidine) phosphoramidite, 5a, was purified on SiO$_2$ (3% MeOH/5%Et$_3$N/toluene) which gave 5.21 g (74.3%) of pure phosphoramidite. $^{31}$P NMR (CD$_3$CN) δ 164.8, 165.4. N$^4$-Benzoyl-3'-(trityl) amino-2',3'-dideoxycytidine-5'-(2-cyanoethyl 2,2,6,6-tetramethylpiperidine) phosphoramidite, 5c, was purified on SiO$_2$ (3% MeOH/5% Et$_3$N/toluene) and gave 5.07 g (74.2%) pure product and some mixed fractions. $^{31}$P NMR (CD$_3$CN) δ 164.8, 165.7. N$^2$-Isobutyryl-3'-(trityl)amino-2',3'-dideoxyguanosine-5'-(2-cyanoethyl 2,2,6,6-tetramethylpiperidine) phosphoramidite, 5g, was precipitated from 2 mL of CH$_2$Cl$_2$ into rapidly stirring ethyl ether (40 mL) and hexane (40 mL) at 4° C. under argon to remove the hydrogen phosphoramidate impurity which cannot be removed by column chromatography in this case. The solid was filtered, washed with hexane, and dried in vacuo. This precipitation step was repeated two times and the resulting solid was purified further on SiO$_2$ (10% Et$_3$N/CH$_2$Cl$_2$) and gave 0.89 g (12.8%) pure phosphoramidite product. $^{31}$P NMR (CD$_3$CN) δ 165.2, 165.5. 3'-(Trityl)amino-3'-deoxythymidine-5'-(2-cyanoethyl 2,2,6,6-tetramethylpiperidine) phosphoramidite, 5t, was purified on SiO$_2$ (5% MeOH/5% Et$_3$N/toluene) and afforded 3.33 g (54.8%) pure phosphoramidite. $^{31}$P NMR (CDCl$_3$) δ 165.3, 166.1.

EXAMPLE 7

Preparation of 3'-(trityl)amino-2',3'-dideoxynucleoside-5'-succinylates, 6a, 6c, and 6t To 1.5 mmol 3'-(trityl)amino-2',3'-dideoxynucleoside (3t, 3c, or 3a) in 5 mL CH$_2$Cl$_2$ was added 0.22 g (1.8 mmol) of N,N-dimethylaminopyridine and then 0.18 g (1.8 mmol) of succinic anhydride. After stirring at room temperature for 1 hour the reaction was quenched by addition of 0.6 mL of methanol, diluted with CH$_2$Cl$_2$ and extracted with cold 10% citric acid, water, and saturated. aq. NaCl. The organic layer was dried (Na$_2$SO$_4$), filtered, and concentrated to a foam. N$^6$-Benzoyl-3'-(trityl)amino-2'-3'-dideoxyadenosine-5'-succinylate, 6a. Yield 1.15 g (100%). N$^4$-Benzoyl-3'-(trityl)amino-2',3'-dideoxycytidine-5'-succinylate, 6c. Yield 0.77 g (76.3%). 3'-(Trityl)amino-3'-deoxythymidine-5'-succinylate, 6t. Yield 0.82 g (94.0%).

EXAMPLE 8

Preparation of 3'-(trityl)amino-2',3'-dideoxynucleoside-5'-succinyl-loaded CPG

To 1 mmol 3'-(trityl)amino-2',3'-dideoxynucleoside-5'-succinylate (6a, 6c or 6t) and 0.13 g (0.95 mmol) of 1-hydroxybenzotriazole in 5 mL N-methylpyrrolidine and 5 mL DMSO was added 0.35 mL (2.0 mmol) of N,N-diisopropylethylamine and then 0.36 g (0.95 mmol) of 2-(1H-benzotriazol-1-yl)-1,1,3,3-tetramethyluronium hexafluorophosphate. The solution was stirred 5 min, added to 10.0 g aminopropyl-CPG, and put on the shaker for 6 hours. The CPG was filtered and washed with DMF, methanol, and ethyl ether. Unreacted amino groups on the CPG were acetylated using the standard ABI capping solutions for 30 min. The nucleoside loadings, determined by trityl assay at 432 nm in 20% TFA/CHCl$_3$ using a molar extinction coefficient of 40.7 $\mu$mol$^{-1}$ cm$^{-1}$, were 38.6 $\mu$mol/g for A, 33.6 $\mu$mol/g for C and 29.0 $\mu$mol/g for T.

EXAMPLE 9

Measurement of the Tetrazole Activation Equilibrium Constant $K_1$

The equilibrium represented by Equation 1 was studied by dissolving N$^6$-benzoyl-3'-tritylamino-deoxyadenosine-5'-(2-cyanoethyl N,N-diisopropyl) phosphoramidite, (4a, 56.1 mg, 70.4 $\mu$mol) in 0.300 mL of dry deuteroacetonitrile and adding 0.300 mL of a solution of 0.5M tetrazole in acetonitrile, all under an argon atmosphere. The solution was transferred to an NMR tube under argon. After 2 min, the $^{31}$P-NMR spectrum shown in FIG. 1 was recorded.

The spectrum consists of resonances corresponding to the phosphoramidite monomer (143.07, 143.72 ppm) the tetrazolidyl-amidite intermediate (127.58 ppm), the hydrogen phosphonate (10.24, 9.61 ppm) resulting from hydrolysis of some of the monomer (through the tetrazolidyl amidite intermediate), and minor side-reactions. The total of the integrations of these species was assumed to be equal to the initial phosphoramidite concentration of 0.1073M, and the concentrations at equilibrium were calculated from the relative integrations of the individual resonances. The concentrations of the species which contain no phosphorus, and therefore do not appear in the spectrum, were calculated as follows. The concentration of the diisopropylammonium tetrazolide at equilibrium (0.0891M) was assumed to be equal to the initial concentration (0.1073M) minus the equilibrium concentration (0.0182M) of the phosphoramidite monomer. The tetrazole concentration at equilibrium (0.0761M) was assumed to be equal to the initial tetrazole concentration (0.2286M) minus the sum of the tetrazolidyl amidite intermediate concentration (0.0634M) and the diisopropylammonium tetrazolide concentration (0.0891M). The activation equilibrium constant $K_1$ was calculated as follows:

$$K_1 = [\text{Tetrazolidyl amidite}] \frac{[R_2NH_2^+ \text{ tetrazolide}^-]}{[\text{Tetrazole}]^2 [\text{monomer amidite}]}$$

$$= \frac{(0.0634 \text{ M}) (0.0891 \text{ M})}{(0.0761 \text{ M})^2 (0.0182 \text{ M})}$$

$$= 53.6 \text{ M}^{-1}$$

Figure 2:
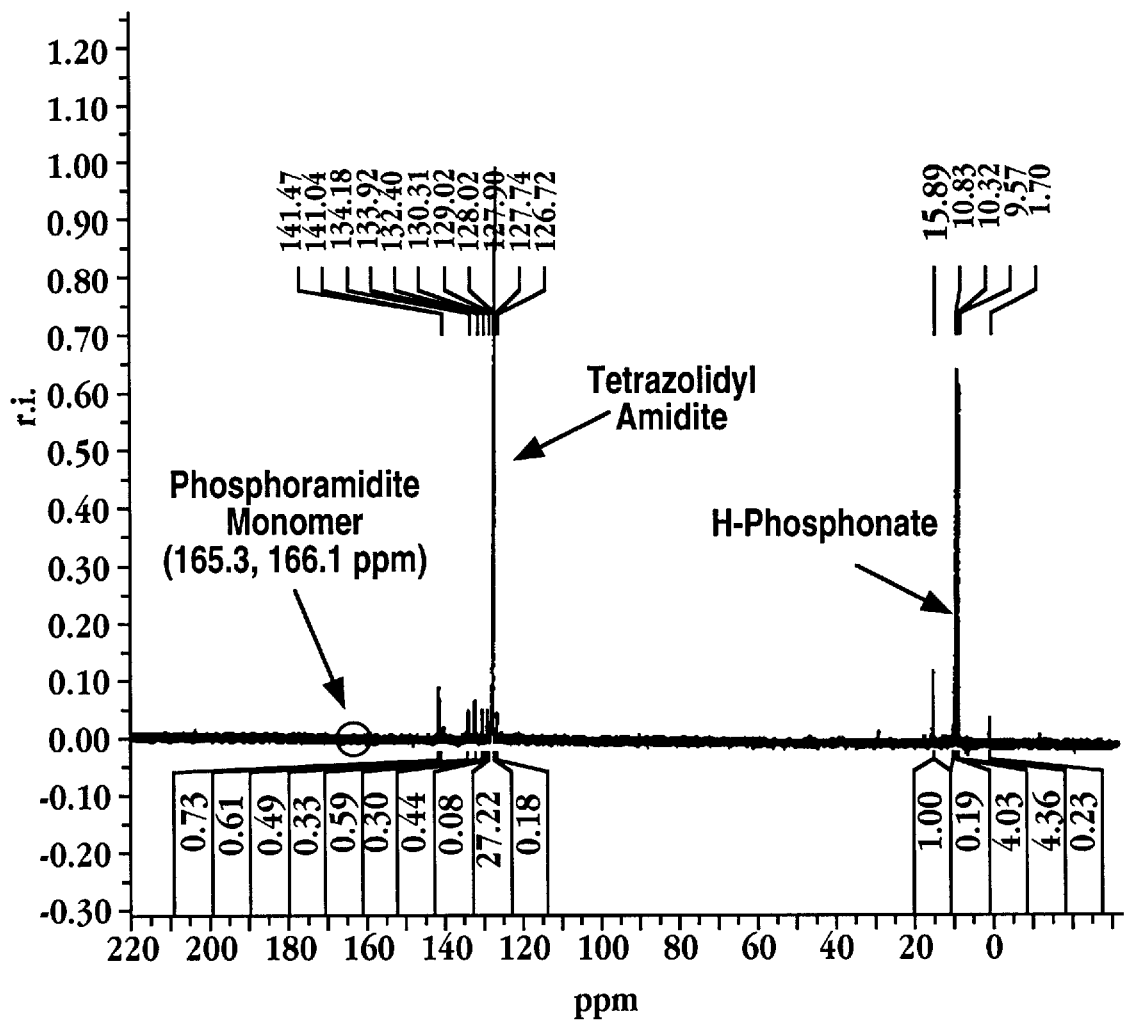
FIG. 2 is a $^{31}$P-NMR spectrum of a mixture of 3'-tritylaminothymidine-5'-(2-cyanoethyl-(2,2,6,6-tetramethylpiperidinyl))-phosphoramidite and tetrazole.

The above experiment was repeated using the 3'-tritylaminothymidine-5'-diisopropylaminophosphoramidite monomer (4t) and the $K_1$ was found to be 56.2 M$^{-1}$. The experiment was repeated again using the 3'-tritylaminothymidine-5'-tetramethylpiperidinyl phosphoramidite monomer (5t). The $^{31}$P-nmr spectrum appears in FIG. 2.

Under the conditions of the experiment, no tetramethylpiperidinyl phosphoramidite monomer remaining at equilibrium (expected at 165.3, 166.1 ppm) was detected. The monomer should be detectable above the noise level of the spectrum if its concentration were at least 0.19 mM. From this information, it may be calculated that the $K_1$ for this equilibrium must be at least 5260 M$^{-1}$, or 93 times greater than that for the diisopropylaminophosphoramidite monomer. The experiment was repeated once more using the 3'-tritylaminothymidine-5'-(N-isopropyl-N-t-butyl) phosphoramidite monomer. As in the case of the tetramethylpiperidinyl phosphoramidite monomer, this monomer was not detectable at equilibrium in the $^{31}$P-NMR spectra.

EXAMPLE 10

1-$\mu$mol Scale Synthesis of Oligo-2'-deoxynucleoside N3'→P5' phosphoramidates using Diisopropylaminophosphoramidite Monomers Oligonucleotide N3'→P5' phosphoramidates were prepared on an ABI 392 DNA synthesizer at the 1-$\mu$mol scale and purified by preparative ion exchange chromatography. The synthesis is performed in the 5' to 3' direction (instead of the 3' to 5' direction which commercially available synthesizers are programmed for) using 1 $\mu$mol of 3'-(trityl)amino-2',3'-dideoxynucleoside-5'-succinyl-loaded CPG in the column. 3'-Tritylamino -5'-diisopropylphosphoramidite monomers were prepared as 0.1M solutions in acetonitrile; the activation solution was 0.5M tetrazole in acetonitrile (PE Applied Biosystems, Foster City, Calif.); the detritylation solution was 3% dichloroacetic acid (DCA) in dichloromethane (DCM), and the oxidation solution was 0.1M iodine in tetrahydrofuran/pyridine/water, 75/20/2, v/v/v solution (PE Applied Biosystems, Foster City, Calif.).

Oligonucleotide N3'→P5' phosphoramidates were synthesized utilizing a repetitive synthesis cycle consisting of detritylation followed by a coupling, oxidation, coupling, oxidation strategy. Detritylation of the 3' amine of the support-bound nucleoside was achieved using a 40 second flow of 3% DCA/DCM for G and A nucleosides and 50 seconds for T and C nucleosides. The support-bound 3'-aminonucleoside was then washed six times with a 10 second acetonitrile delivery/5 second argon flush combination. Coupling of the amine with the 5'-phosphoramidite-3'-tritylamino nucleoside was achieved using an alternating delivery to the column of monomer plus tetrazole and tetrazole alone for ~10 seconds followed by a 5 minute wait. The monomer was flushed from the column with argon and the iodine solution was immediately added, followed by a 2 minute wait. Upon completion of oxidation the growing support bound oligomer was washed one time with a 20 second acetonitrile delivery/5 second argon flush combination and five times with a 10 second acetonitrile delivery/5 second argon flush combination. Coupling and oxidation were repeated one additional time followed by washing prior to detritylation. Using this procedure ~15 equivalents (compared to initial loading of support-bound nucleoside) of monomer is used for each coupling step; therefore ~30 equivalents monomer is used for each synthesis cycle.

Upon synthesis completion, the support-bound 3'-detritylated oligonucleotide N3'→P5' phosphoramidate was cleaved and base-deprotected in concentrated aqueous ammonia at 55° for 12 hours. The cleaved and deprotected oligonucleotide N3'→P5' phosphoramidate solution was removed from the CPG and the CPG was washed 2 times with 200 $\mu$l of ammonia. All the ammonia washes were combined, the solution was buffered to 0.01M NaOH and the ammonia was removed under vacuum. Following filtration, the crude oligonucleotide was purified on a preparative anion exchange column (Pharmacia MonoQ 10/10), desalted on Sephadex G-25 (Pharmacia NAP-5), and lyophilized.

Figure 3A:
FIGS. 3a and 3b are ion exchange chromatograms of two crude oligonucleotide N3'→P5' phosphoramidates synthesized by the amine-exchange reaction of the invention.
Figure 3B:
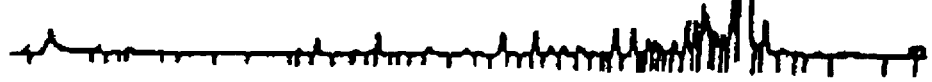

The sequences listed below were synthesized on an ABI 392 synthesizer using either the phosphoramidite amine exchange method of the invention or the Atherton-Todd oxidative coupling approach, e.g as described in Letsinger et al, U.S. Pat. No. 5,476,925. Results are tabulated below and illustrated in FIGS. 3a and 3b, which show chromatograms of ion-exchange HPLC separations of the two mixed-base sequences listed in the table.

| Sequence[1] | SEQ ID NO: | Method | Crude OD | x | HPLC Purity | = | Yield (OD units) |
|---|---|---|---|---|---|---|---|
| $T_{15}$ | 3 | Amine exchange | 74 | | 56% | | 41 |
| $T_{15}$ | 3 | Atherton-Todd | 49 | | 29% | | 14 |
| $A_{15}$ | 4 | Amine exchange | 101 | | 39% | | 39 |
| $A_{15}$ | 4 | Atherton-Todd | 86 | | 8% | | 7 |
| 5'-AACGAGTTGGGGCAT | 5 | Amine exchange | 96 | | 42% | | 40 |
| 5'-TTCTCTCTCTA | 6 | Amine exchange | 71 | | 62% | | 44 |

[1]Sequences synthesized by the Atherton-Todd oxidative coupling method have a 3'-terminal hydroxyl group whereas the sequences synthesized by the amine exchange method have a 3'-terminal amino group.

EXAMPLE 11

1-μmol Scale Synthesis of Oligo-2'-deoxynucleoside N3'→P5 Phosphoramidates using Diisopropylaminophosphoramidite Monomers: Comparison of Couple/Oxidation to Couple/Oxidation/couple/oxidation The effect on product yield of a single couple/oxidation step was compared with that of a double couple/oxidation step (couple/oxidation/couple oxidation) as follows: The sequence 5'-AAC-ATG-GAG-AGC-GTC-3' (SEQ ID NO: 7) was synthesized using diisopropylamino phosphoramidite monomers using the procedure described above and compared to a second synthesis which was like that above, but with the following exceptions: 1) a single couple/oxidation was used per cycle (instead of two), and 2) the concentration of monomer solution was 0.2M (instead of 0.1M). Therefore in the single couple /oxidation experiment 30 equivalents of monomer were used in each synthesis cycle, whereas in the couple/oxidation/couple/oxidation experiment ~15 equivalents of monomer were used in each of the two coupling steps, for the same total of ~30 equivalents of monomer per synthesis cycle. The results, which appear below, demonstrate the improved efficiency using the 2x (couple/oxidation) method.

| Method | Crude OD | x | HPLC Purity | = | Yield (OD units) |
|---|---|---|---|---|---|
| Couple/oxidation | 113 | | 21.3% | | 24.1 |
| 2 x (Couple/oxidation) | 115 | | 29.4% | | 33.8 |

EXAMPLE 12

1-μmol Scale Synthesis of oligo-2'-deoxynucleoside N3'→P5' Phosphoramidates: Comparison of No Capping, Acetic Anhydride Capping and Isobutyric Anhydride Capping The sequence 5'-AAC-ATG-GAG-AGC-GTC-3' (SEQ ID NO: 7) was synthesized three times on a 1-μmol scale using the above procedure, but in two of the syntheses a 60 second capping step was inserted after the last oxidation step and before detritylation in each cycle. Acetic anhydride/NMI (PE Applied Biosystems, Foster City, Calif.) were used as capping reagents in one of the experiments and isobutyric anhydride (1/1/8 isobutyric anhydride/2,6-lutidine/THF)/NMI (PE Applied Biosystems, Foster City, Calif.) was used in the other. The results which appear below demonstrate the improved yield and purity with capping.

| Capping Procedure | Crude OD | x | HPLC Purity | = | Yield (OD units) |
|---|---|---|---|---|---|
| No Capping | 97 | | 29.6% | | 28.7 |
| Acetic Anhydride | 97 | | 39.6% | | 38.4 |
| Isobutyric Anhydride | 82 | | 39.6% | | 32.5 |

EXAMPLE 13

1-μmol Scale Synthesis of oligo-2'-deoxynucleoside N3'→P5' Phosphoramidates: Comparison of $I_2$ and $H_2O_2$ Oxidation The following sequences were synthesized on a 1-μmole scale using the above procedure, however in one set of experiments the iodine oxidation reagent was replaced with an oxidizing agent consisting of 1.5% $H_2O_2$/3.5% $H_2O$/20% pyridine/75% THF. No capping was employed in these experiments.

| Sequence | Oxidizing Agent | % Full Length Product | % "N-1" Failure Sequences |
|---|---|---|---|
| 5'-TTTTT | $I_2$ | 76.94 | 5.11 |
| 5'-TTTTT | $H_2O_2$ | 80.05 | 2.55 |
| 5'-TAAAA | $I_2$ | 73.05 | 4.28 |
| 5'-TAAAA | $H_2O_2$ | 78.72 | 2.69 |

EXAMPLE 14

10-μmol Scale Synthesis of oligo-2'-deoxynucleoside N3'→P5' Phosphoramidates: Comparison of Diisopropyl and Tetramethylpiperidinyl Phosphoramidite Monomers The following general procedure was followed for 10-μmol-scale synthesis: Oligonucleotide N3'→P5' phosphoramidates were prepared on a modified 390Z ABI DNA synthesizer at the 10-μmol scale and purified by preparative ion exchange chromatography. 3'-Tritylamino 5'-phosphoramidite monomers were prepared as 0.1M solutions in acetonitrile; the activator was 0.15M tetrazole in acetonitrile; the detritylation solution was 3% dichloroacetic acid (DCA) in dichloromethane (DCM), and the oxidation solution was 0.1M iodine in tetrahydrofuran/pyridine/water, 75/20/2 (v/v/v) (PE Applied Biosystems, Foster City, Calif.).

Oligonucleotides were synthesized utilizing a batch-mode repetitive synthesis cycle consisting of detritylation followed by coupling and oxidation. Individual modules were written and combined to form the complete synthesis cycle. More specifically, the synthesis is performed in the 5' to 3' direction using 10 μmol of 3'-(trityl)amino-2',3'- dideoxynucleoside-5'-succinyl-loaded CPG. Detritylation of the 3'-amine was achieved using a repetitive flow of 3% DCA/DCM to the top of the reaction vessel followed by a 3 second vortex and drain. The total acid exposure time is approximately 2 minutes. The support-bound 3'-aminonucleoside was then washed 10 times with a series of alternating washes from the bottom of the reaction vessel as well as from the top with vortexing and draining. Coupling of the resulting free amine (presumably as its dichloroacetate salt) with the 3'-(trityl)aminonucleoside-5'-phosphoramidite monomer was performed using an initial delivery of monomer to the reaction vessel followed by the delivery of tetrazole. The coupling mixture was then vortexed for 5 minutes. After draining the reaction vessel, the iodine solution was immediately added, and vortexed for 2 minutes. The oxidation solution was drained and the support was washed 10 times with a series of alternating acetonitrile washes from the bottom of the reaction vessel as well as from the top with vortexing and draining.

Upon completion of the synthesis, the 3'-deprotected oligonucleotide was cleaved from the support and deprotected with concentrated aqueous ammonia at 55° for 12 hours. The solution was buffered to 0.01M NaOH and the ammonia removed under vacuum. Following filtration, the crude solution was purified on a preparative anion-exchange column (Pharmacia MonoQ 10/10), desalted, and lyophilized.

Using the above method, 5'-TT-3' dimers were synthesized on the 10 μmole scale using varying concentrations (and therefore varying number of equivalents) of tetrazole and of either the diisopropylamino phosphoramidite monomer or the tetramethylpiperidine phosphoramidite monomer. The results clearly indicate that phosphoramidate synthesis can be performed using significantly lower equivalents of the more potent tetramethylpiperidinyl phosphoramidite monomer than the less potent diisopropylamino phosphoramidite monomer.

| Type of Monomer | Monomer Equivalents | Tetrazole Equivalents | % Dimer | % Unreacted Monomer |
|---|---|---|---|---|
| diisopropyl | 10 | 50 | 93.8 | 2.4 |
| diisopropyl | 5 | 50 | 89.1 | 5.0 |
| diisopropyl | 2.8 | 28 | 87.1 | 8.0 |
| diisopropyl | 2.8 | 7 | 82.9 | 14.0 |
| tetramethyl-piperidine | 2.8 | 7 | 94.2 | 2.8 |

EXAMPLE 15

10-μmol Scale Synthesis of oligo-2'-deoxynucleoside N3'→P5' Phosphoramidates

The following sequences were synthesized on the 10-μmole scale using the above procedure and using the following quantities of tetramethylpiperidinyl phosphoramidite monomers.

| Sequence | Monomer Equivalents per cycle | HPLC Yield (%) |
|---|---|---|
| 5'-TT[1] | 4 | 94.0 |
| 5'-AA[1,2] | 4 | 98.1 |
| 5'-CC[1,2] | 4 | 96.9 |
| 5'-CCC[2] | 4 | 93.2 |
| 5'-TTTTT | 2.8 | 82.7 |

[1]This oligo was cleaved from the support with the terminal trityl group remaining on the dimer.
[2]This HPLC yield is corrected for the benzamide formed from deprotection of the benzoyl protecting group on the base.

EXAMPLE 16

$N^4$-benzoyl-2'-fluoro-3'-(4-methoxytrityl)amino-2', 3'-dideoxyuridine 5'-(2-cyanoethyl N,N-diisopropyl Phosphoramidite 2'-Fluoronucleoside phosphoramidite monomers of the invention are prepared as illustrated in Schemes V and VI. Briefly, a ribonucleoside is transformed into a 5'-hydroxyl-protected-2',3'-anhydroxylnucleoside, after which the 2',3'-epoxy ring is opened by treatment with sodium azide, or like reagent, to form a 5'-hydroxyl-protected-3'-azido-3'-deoxyarabinonucleoside. After purification, the 5'-hydroxyl-protected-3'-azido-3'-deoxyarabinonucleoside is fluorinated at the 2' position by treatment with diethylaminosulfur trifluoride (DAST), or like reagent, after which the azido group is reduced to give a 3'-amino. After suitably protecting the 3'-amino and releasing the 5'-hydroxyl protecting group, the nucleoside is phosphitylated at the 5' oxygen to give the crude phosphoramidite monomer.

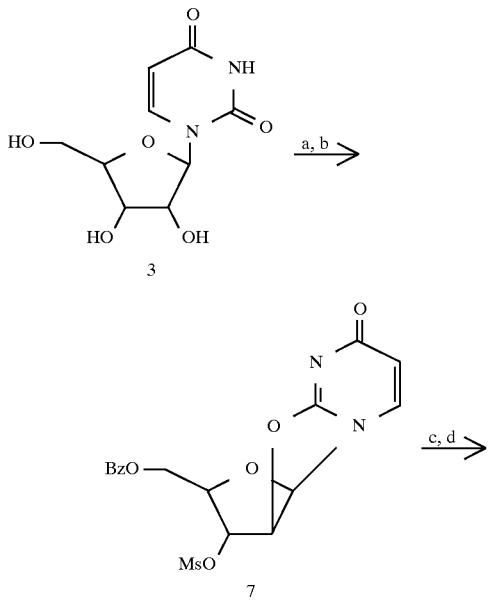

Scheme V

Scheme V -continued

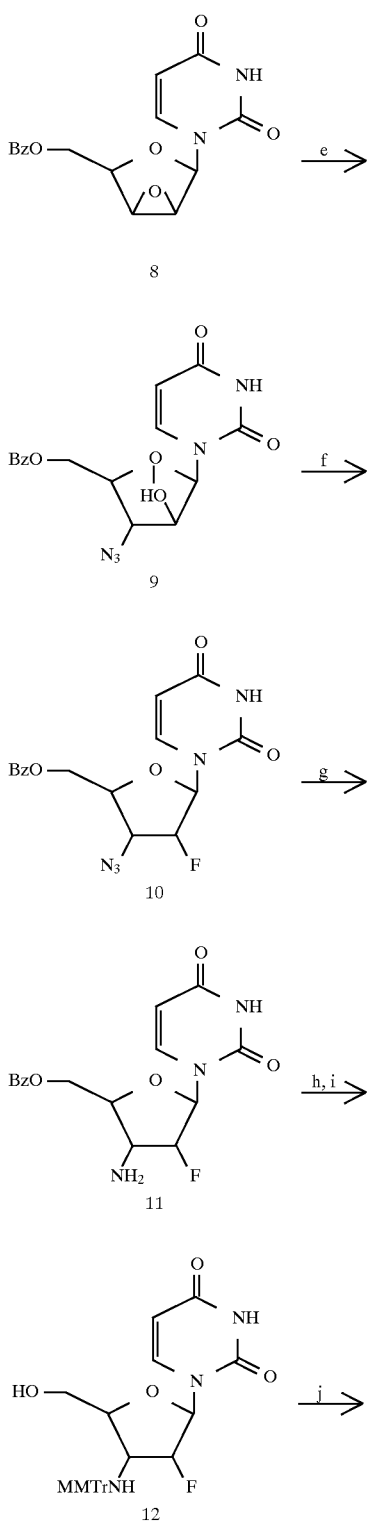

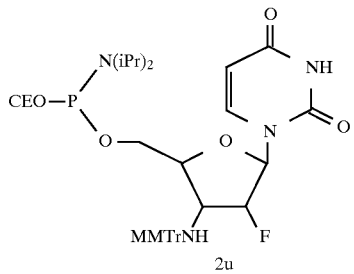

a) MsCl
b) NaOBz
c) HCl, H₂O
d) NH₄OH
e) NH₄N₃
f) DAST
g) H₂, Pd/C
h) MMTrCl
i) NaOH, H₂O
j) CEOP(N(iPr)₂)₂

In reference to Scheme V, uridine 3 was mesylated and then selectively benzoylated with accompanying formation of the 2,2'-anhydrocycle by treatment with sodium benzoate according to literature procedure, e.g. Codington, J. F.; Fecher, R.; Fox, J. J. J Am. Chem. Soc. 1960, 82, 2794–2803. These reactions resulted in compound 7 with 69–77% overall yields. By another literature method (Codington, J. F.; Fecher, R.; Fox, J. J. J Organic Chem. 1962, 27, 163–167), 2,3'-anhydroarabinonucleoside 7 was transformed into 2',3'-anhydrolyxouridine 8 in two steps. This involved treatment of 7 with hydrochloric acid to form 3'-mesyl-5'-benzoylarabinouridine, which upon treatment with ammonium hydroxide closed to form the lyxo-2',3'-epoxide 8 in 63–77% overall yields. Then, also according to published procedure (Reichman, U.; Hollenberg, D. H.; Chu, C. K.; Watanabe, K. A.; Fox, J. J. *J. Organic Chem.* 1976, 41, 2042–2043), 2',3'-anhydrolyxonucleoside 8 was heated with ammonium azide. Contrary to literature suggestion, this reaction was not completely stereoselective, but produced a chromatographically unresolvable mixture of the desired 5'-benzoyl-3'-azidoarabinonucleoside 9 and it's 2'-azido-2'-deoxyregioisomer 9i in approximately a 2.5:1 ratio. Crude arabinonucleoside 9 was fluorinated with DAST to give 2'-fluoro-3'-azidonucleoside 10, then catalytically hydrogenated to give 2'-fluoro-3'-aminonucleoside 11, which was separable from its regioisomer by silica gel chromatography. Protection of the 3'-amine with a monomethoxytrityl (MMT) group, followed by 5'-debenzoylation produced intermediate 13, with 5'-phosphitylation producing the desired phosphoramidite building block 2u in a 22% overall yield from anhydronucleoside 8. More particularly, the steps were carried out as follows:

3'-O-Methanesulfonyl-5'-O-benzoyl-2,2'-anhydroarabinouridine 7 was prepared in two steps from 3 according to the procedure of Codington et al. (cited above, J. Am. Chem. Soc.) in 69–77% overall yields.

5'-O-benzoyl-2',3'-anhydrolyxouridine 8 was prepared in two steps from 7 according to the procedure of Codington et al. (cited above, J. Organic Chem.) in 63–77% overall yields.

3'-azido-5'-O-benzoyl-3'-deoxyarabinouridine 9 was prepared from 8 and anhydrous $NH_4N_3$ (described in Obenland, C. O.; Mangold, D. J.; Marino, M. P. *Inorg. Synth.* 1966, 8, 53–56) according to the procedure of Reichman et al., (cited above) but without successful recrystallization. Mass yields were 98% or greater, but NMR suggested 25–35% of the regioisomer, 2'-azido-5'-O-benzoyl-2'-deoxyxylouridine, 9i, which co-eluted with the desired product by silica gel TLC. $^1H$ NMR, Major component, 9: δ 10.8 (br s, 1H), 8.11 (d, J=7.5 Hz, 2H), 7.68 (d, J=8.1 Hz, 1H), 7.62 (d, J=7.3 Hz, 1H), 7.5 (m, 2H), 6.19 (d, J=3.6 Hz, 1H), 5.40, (d, J=8.0 Hz, 1H), 4.84 (m, 1H), 4.73 (d, J=5.7 Hz, 1H), 4.63 (br d, J=4.2 Hz, 1H), 4.2 (mm, 2H); Minor component, 9i: δ 10.6 (br s, 1H), 8.11 (d, J=7.5 Hz, 2H), 7.81 (d, J=8.1 Hz, 1H), 7.64 (d, J=7.5 Hz, 1H), 7.5 (m, 2H), 5.85 (s, 1H), 5.47, (d, J=8.1 Hz, 1H) 4.86 (m, 1H), 4.76 (d, J=5.4 Hz, 1H), 4.62 (br d, J=4.0 Hz, 1H), 4.3–4.2 (mm, 2H).

2'-fluoro-3'-azido-5'-O-benzoyl-2',3'-dideoxyuridine 10 was prepared as follows: To 5.0 g (13.4 mmol) of crude 9 (containing 25% 9i) in 30 mL anhydrous $CH_2Cl_2$ was added 8.8 mL (66.6 mmol) of diethylaminosulfur trifluoride. After stirring for 48 h, the mixture was diluted with 100 mL $CH_2Cl_2$ and poured into 200 mL saturated aqueous $NaHCO_3$. When evolution of gas ceased, the $CH_2Cl_2$ layer was washed with 100 mL fresh $NaHCO_3$ solution and then with water (2×100 mL). Concentration of the $CH_2Cl_2$ layer in vacuo and flash chromatography gave 3.5 g (70%) of product containing 20% of the largely chromatographically unresolvable isomeric impurity, 10i. $^1H$ NMR, Major component, 10: δ 8.7 (br s, 1H), 8.07 (d, J=7.4Hz, 2H), 7.62 (d, J=7.5 Hz, 1H), 7.49 (dd, J=7.6, 7.6 Hz, 2H), 7.39 (d, J=8.1 Hz, 1H), 5.70 (d, J=21.1 Hz, 1H), 5.65 (d, J=8.2 Hz, 1H), 5.48 (dd, J=4.7, 52.9 Hz, 1H), 4.7–4.4 (unresolved), 4.32 (dd, J=4.7, 9.5 Hz, 1H), 4.27 (dd, J=4.7, 9.5 Hz, 1H); Minor component, 10i: δ 8.7 (br s, 1H), 8.03 (d, J=7.2 Hz, 2H), 7.64 (d, J=7.6 Hz, 1H), 7.51 (dd, J=7.4, 7.7 Hz, 2H), 7.33 (d, J=8.2 Hz, 1H), 5.99 (d, J=6.4 Hz, 1H), 5.67 (d, J=9 Hz, 1H), 5.40 (ddd, J=2.8, 5.0, 53.4 Hz, 1H), 4.8–4.4 (unresolved), 4.10 (mm, 2H).

2'-fluoro-3'-amino-5'-O-benzoyl-2',3'-dideoxyuridine 11 was prepared as follows: To 3.5 g (9.3 mmol) crude 10 (20% 10i) in 200 mL 95% ethanol was added 600 mg of 10% palladium on carbon. The suspension was hydrogenated at 40 psi overnight and then the catalyst removed by filtration. The solvent was removed in vacuo, giving 2.93 g (90%) of a light yellow solid consisting of two compounds which were resolvable by TLC. Flash chromatography provided 1.96 g (60% yield) of the desired product as a pure white solid. Mass-spectrometry, $FAB^+$, $M+H^+$, calculated: 350.1152, observed: 350.1152. $^1H$ NMR δ 8.14 (br s, 1H), 8.06 (d, J=7.1 Hz, 1H), 7.64 (dd, J=7.4, 7.4 Hz, 1H), 7.57 (d, J=8.2 Hz, 1H), 7.50 (dd 7.7, 7.8 Hz, 1H), 5.86 (d, J=18.5 Hz, 1H), 5.51 (d, J=8.2 Hz, 1H) 5.00 (dd, J=4.3, 52.4 Hz, 1H), 4.8 (dd J=2.2, 12.8 Hz, 1H), 4.73 (dd, J=3.5, 12.7 Hz, 1H), 4.14 (ddd, J=2, 3, 10.2 Hz, 1H), 3.57 (ddd, J=4, 10.5, 26.6 Hz, 1H); $^{19}F$ NMR δ–198.3 (ddd, J=18.5, 26.4, 52.2 Hz).

2'-fluoro-3'-(4-methoxytrityl)amino-2',3'-dideoxyuridine 12 was prepared as follows: To 1.0 g (2.9 mmol) of 11 in 50 mL anhydrous pyridine was added 1.0 g (3.2 mmol) 4-methoxytrityl chloride. The mixture was stirred overnight, 5 mL saturated aqueous $NaHCO_3$ was added, and the mixture concentrated in vacuo to an oil. The oil was dissolved in 125 mL ethyl acetate, which was washed with water (3×100 mL) and reconcentrated in vacuo to 2.05 g of foam.

The foam was dissolved in a mixture of 40 mL methanol, 40 mL dioxane, and 10 mL water. NaOH (1 g, 25 mmol) was added and the mixture stirred overnight. The solution was concentrated in vacuo to a syrup, which was dissolved in 100 mL ethyl acetate and washed with water (3×100mL). Concentration in vacuo of the organic layer gave 1.11 g of a foam, which upon flash chromatography gave 1.05 g (76%) of a white solid. Mass-spectrometry, $FAB^+$, $M+H^+$, calculated: 518.2091, observed: 518.2076. $^1H$ NMR δ 8.64 (br d J=4.2 Hz, 1H), 8.14 (br s, 1H), 7.57 (mm, 5H), 7.48 (d J=8.7 Hz, 1H), 7.3 (mm, 8H), 6.83 (d J=8.8 Hz, 2H), 5.67 (d, J=17.7 Hz, 1H), 5.62 (d, J=8.1 Hz, 1H), 4.23 (m, 2H), 4.03 (br d, J=10.2 Hz, 1H), 3.80 (s, 3H), 3.31 (dddd, J=3.6, 10.3, 10.9, 25.8 Hz, 1H), 2.80 (dd, J=3.6, 50.9 Hz, 1H), 2.51 (dd, J=3.0, 11.2 Hz, 1H); $^{19}F$ NMR δ–192.5 (dddd, J=2.9, 17.7, 26.1, 50.9 Hz).

$N^4$-benzoyl-2'-fluoro-3'-(4-methoxytrityl)amino-2',3'-dideoxyuridine 5'-(2-cyanoethyl N,N-diisopropyl) phosphoramidite 2u was prepared as follows: To 700 mg (1.35 mmol) of 12 in 20 mL anhydrous $CH_2Cl_2$ was added 200 mg (1.17 mmol) of diisopropylammonium tetrazolide and 0.5 mL (1.57 mmol) of 2-cyanoethyl N,N,N',N'-tetraisopropylphosphorodiamidite. After stirring the mixture for 3h, the solvent was removed in vacuo and the residue purified on a Chromatotron, using 4 mm plates and eluting with 0–3% methanol, 0.5% triethylamine in $CH_2Cl_2$. The product was concentrated in vacuo to an oil, which was dissolved in 10 mL $CH_2Cl_2$ and precipitated by slow addition into 100 mL of rapidly stirred hexane. After decanting the supernatant, the product was vacuum desiccated over $P_2O_5$, giving 680 mg (70%) of white powder. Mass-spectrometry, $FAB^+$, $M+H^+$, calculated: 718.3170, observed: 718.3194. $^{19}F$ NMR δ –190.9 (ddd, J=21.7, 21.8, 51.3 Hz); $^{31}P$ NMR δ 150.5, 149.5.

EXAMPLE 17

$N^4$-benzoyl-2'-fluoro-3'-(4-methoxytrityl)amino-2',3'-dideoxycytidine 5'-(2-cyanoethyl N,N-diisopropyl)phosphoramidite Crude intermediate 10 was used for preparation of the appropriately protected cytidine phosphoramidite 2c as shown in Scheme VI below. The uracil base of 10 was converted to cytosine by adaptation of the method of Divakar and Reese, *J. Chem. Soc., Perkin. Trans.* 1 1982, 1171–1176. Subsequent 4-N benzoylation and reduction of the 3'-azido to an amino group gave compound 13, which was separable from its regioisomer by silica gel chromatography. Protection of the 3'-amine with an MMT group, followed by selective 5'-O-debenzoylation produced intermediate 15. Subsequent 5'-phosphitylation lead to desired phosphoramidite 2c in a 10% overall yield based on anhydronucleoside 8.

Scheme VI

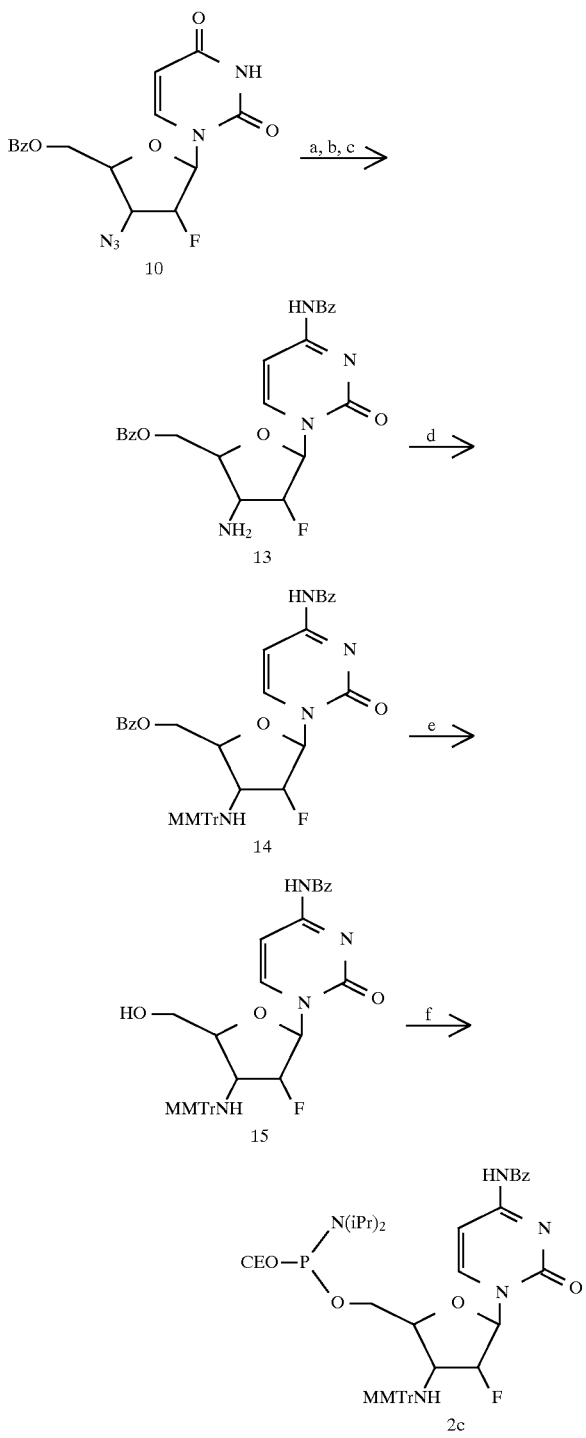

a) POCl₃, triazole, TEA; NH₄OH
b) BzCl
c) H₂, Pd/C
d) MMTrCl
e) NaOH, Pyr/MeOH/H₂O; H⁺-Pyr dowex
f) CEOP(N(iPr)₂)₂

More particularly, the steps were carried out as follows: $N^4,5'$-O-dibenzoyl-2'-fluoro-3'-amino-2',3'-dideoxycytidine 13 was prepared as follows: To 6.9 g (18.4 mmol) of crude 10 (containing 35% 10i) in 50 mL anhydrous CH₃CN was added an ice-cold solution of 11.7 g (169 mmol) 1,2,4- triazole and 3.35 mL (36.1 mmol) POCl₃ in 90 mL anhydrous CH₃CN. The mixture was cooled in an ice bath and anhydrous triethylamine (23 mL, 165 mmol) was added, then the reaction allowed to warm to room temperature with stirring. After 90 min, 15 mL (108 mmol) triethylamine and 4 mL water were added and the mixture stirred for 10 min. The solvent was removed in vacuo, then 250 mL ethyl acetate was added, and the solution was TLC indicated a fluorescent intermediate with the same mobility as the starting material.

The mixture was concentrated in vacuo to 6.7 g of a foam. Dioxane (100 mL) and 20 mL concentrated aqueous ammonia were added, and after 3 h, the mixture was concentrated in vacuo to a yellow gel. The gel was dissolved in 100 mL ethyl acetate and washed with water (3×200 mL). Concentration in vacuo and vacuum desiccation over P₂O₅ yielded 5.4 g of a solid which gave only one spot by silica gel TLC. Only two significant signals were observed by $^{19}F$ NMR, Major component: 67 –192.8 (ddd, J=22.8, 22.8, 53.1 Hz); Minor component: δ –200.7 (ddd, J=13.6, 19.9, 53.4 Hz).

Anhydrous pyridine (100 mL) was added and the solution cooled to 4° C. Benzoyl chloride (11.7 mL 100 mmol) was added with stirring and the mixture allowed to warm to room temperature. After 2 h, 5 mL water was added and the solvent removed in vacuo, giving a brown oil, which was dissolved in 200 mL ethyl acetate, washed with water (3×200 mL), and then reconcentrated in vacuo to an oily foam.

Ethanol (150 mL) and 2 g of 10% palladium on activated carbon were added and the mixture was hydrogenated at 40 psi H₂ overnight. TLC indicated formation of two new slower, closely-migrating compounds.

The catalyst was removed by filtration, and the filtrate concentrated in vacuo to an oily yellow foam. Silica gel flash chromatography (500 mL silica, eluted with 0–3% CH₃OH in CH₂Cl₂) provided 1.85 g of semi-pure product, which was dissolved in 10 mL CH₂Cl₂. A solid quickly precipitated, which was collected by filtration and washed with fresh CH₂Cl₂. Vacuum desiccation yielded 1.5 g of product 13 (11% yield from 9 and 9i) as fine white crystals. Mass-spectrometry, FAB⁺, M+H⁺, calculated: 453.1574, observed: 453.1574. ¹H NMR δ 8.21 (d, J=7.5 Hz, 1H), 8.08–8.13 (mm, 3H), 7.94 (d, J=7.4 Hz, 2H), 7.46–7.7 (mm, 8H), 6.04 (d, J=16.9 Hz, 1H), 5.08 (dd, J=3.6, 51.5 Hz, 1H), 4.85 (dd, J=3.3, 12.8 Hz, 1H), 4.80 (dd, J=2.1, 12.8 Hz, 1H), 4.26 (m, 1H), 3.48 (dm, J=27 Hz, 1H); ¹⁹F NMR δ –200.1 (m).

$N^4,5'$-O-dibenzoyl-2'-fluoro-3'-(4-methoxytrityl)amino-2',3'-dideoxycytidine 14 was prepared as follows: To 0.9 g (2.0 mmol) of 13 in 25 mL anhydrous pyridine was added 0.86 g (2.8 mmol) 4-methoxytrityl chloride, and the mixture stirred overnight. The reaction was quenched with 0.5 mL H₂O and concentrated in vacuo. CH₂Cl₂ (50 mL) was added and washed with 50 mL saturated aqueous NaHCO₃ and with water (2×50 mL). The solvent was removed in vacuo, replaced with 10 mL CH₂Cl₂, and pipetted into 80 mL rapidly stirred 1/1 hexane/ether. After further stirring for 2 h, the product was collected by filtration and dried under vacuum, giving 1.3 g (88% yield) of product as a white powder. Mass-spectrometry, FAB⁺, M+H⁺, calculated: 725.2775, observed: 725.2761. ¹H NMR δ 8.59 (br s, 1H), 8.07 (br d, J=5.7 Hz, 1H), 7.89 (br d, J=7 Hz, 2H), 7.83 (dd, J=1.3, 6.7 Hz, 2H), 7.68 (dd, J=7.4, 7.4 Hz, 2H), 7.5–7.6 (m, 8H), 7.43 (dd, J=2.1, 6.9 Hz, 2H), 7.1–7.3 (mm, 7H), 6.71 (d, J=8.9 Hz, 2H), 5.80 (d, J=15.4 Hz, 1H), 5.03 (dd, J=2.0, 13.0 Hz, 1H), 4.98 (dd, J=2.3;, 13.1 Hz, 1H),4.41 (brd,J= 10.5 Hz, 1H),3.63 (s,3H),3.36(dddd,J=3.1, 11.1, 11.1, 25.7 Hz, 1H), 2.84 (dd, J=3.1, 49.9 Hz, 1H), 2.52 (dd, J=2.7, 11.5 Hz, 1H); ¹⁹F NMR δ –196.3 (m).

N$^4$-benzoyl-2'-fluoro-3'-(4-methoxytrityl)amino-2',3'-dideoxycytidine 15 was prepared as follows: To 1.3 g (1.75 mmol) of 14 in 20 mL of 65/30/5 pyridine/methanol/water, cooled in an ice bath, was added 10 mL of cold 2M NaOH in 65/30/5 pyridine/methanol/water. The mixture was stirred cold for 20 min, then neutralized with pyridinium-H$^+$ form Bio-Rad AG® 50W-X8 cation exchange resin. After 5 min, the resin was removed by filtration and washed with methanol. The combined filtrate and wash were concentrated in vacuo to an oil, which was dissolved in 100 mL ethyl acetate. The mixture was washed with 100 mL saturated aqueous NaHCO$_3$ and with water (2×100 mL). After concentration in vacuo to a foam, the product was dissolved in 10 mL CH$_2$Cl$_2$ and pipetted into 75 mL rapidly stirred hexane/ether, 2/1. The product was collected by filtration and dried under vacuum, giving 1.13 g (102% yield) of product as a white powder. Mass-spectrometry, FAB$^+$, M+Cs$^+$, calculated: 753.1489, observed: 753.1499. $^1$H NMR δ 8.30 (br d, J=6.8 Hz, 1H), 7.89 (br d, J=6.7 Hz, 2H), 7.64 (dd, J=7.4, 7.4 Hz, 1H), 7.44–7.56 (mm, 9H), 7.22–7.32 (mm, 9H), 6.82 (d, J=8.8Hz, 2H), 5.80 (d, J=15.7Hz, 1H), 4.26 (mm, 2H), 4.13 (d, J=10.2 Hz, 1H), 3.81 (s, 3H), 3.26 (dddd, J=3.4, 10.7, 10.8, 26.5 Hz, 1H), 2.93 (dd, J =3.3, 50.5 Hz, 1H), 2.50 (dd, J=2.8, 11.0 Hz, 1H); $^{19}$F NMR δ –195.3 (m).

N$^4$-benzoyl-2'-fluoro-3'-(4-methoxytrityl)amino-2',3'-dideoxycytidine 5'-(2-cyanoethyl N,N-diisopropyl) phosphoramidite 2c was prepared as follows: To 970 mg (1.56 mmol) of 15 in 25 mL anhydrous CH$_2$Cl$_2$ was added 200 mg (1.17 mmol) of diisopropylammonium tetrazolide and 1.0 mL (3.15 mmol) of 2-cyanoethyl N,N,N',N'-tetraisopropylphosphorodiamidite. After stirring the mixture for 3h, the solvent was removed in vacuo and the residue purified on a Chromatotron, using 4 mm plates and eluting with 0–1.5% methanol in 0.5% triethylamine in CH$_2$Cl$_2$. The product was concentrated in vacuo to a foam, which was dissolved in 10 mL CH$_2$Cl$_2$, and precipitated by slow addition to 40 mL of rapidly stirred hexane. After decanting the supernatant, the product was vacuum desiccated over P$_2$O$_5$, giving 880 mg (69%) of white powder. Mass-spectrometry, FAB$^+$, M+Cs$^+$, calculated: 953.2568, observed: 953.2531. $^{19}$F NMR δ –193.6 (m); $^{31}$P NMR δ 150.4,149.4.

EXAMPLE 18

N$^4$-benzoyl-2'-fluoro-3'-(4-methoxytrityl)amino-2', 3'-dideoxytidine 5'-succinyl-loaded CPG Intermediate 15 was 5'-succinylated and loaded upon CPG solid support by standard procedures, e.g. Atkinson, T.; Smith, M. In *Oligonucleotide Synthesis. A Practical Approach*, Gait, M. J. Ed., IRL Press, 1984, 35–81; and Knorr, R.; Trzeciak, A.; Bannwarth, W.; Gillessen, D. *Tetrahedron Lett.* 1989, 30, 1927–1930. More, particularly, N$^4$-benzoyl-2'-fluoro-3'-(4-methoxytrityl)amino-2',3'-dideoxycytidine 5'-succinyl-loaded CPG was prepared as follows: To 100 mg (0.16 mmol) of 15 in 2 mL anhydrous CH$_2$Cl$_2$ was added 55 mg (0.55 mmol) of succinic anhydride and 65 mg (0.53 mmol) of dimethylaminopyridine. The mixture was stirred for 2 h, the evaporated in vacuo to an oil. The oil was dissolved in 20 mL CH$_2$Cl$_2$, washed with 20 mL of saturated aqueous NaHCO$_3$ and with water (2×20mL), and then reconcentrated in vacuo to a foam. To the foam was added 1 mL 0.4M diisopropylethylamine in DMSO/N-methylpyrrolidine, 1/1, and 0.7 mL 0.2M 1-hydroxybenzotriazole, 0.2M 2-(1H-benzotriazol-1-yl)-1, 1,3,3-tetramethyluronium hexafluorophosphate in DMSO/N-methylpyrrolidine, 1/1. After 3 min, the mixture was drawn into a 10 mL syringe containing 1.2 g of long-chain alkylamino-CPG. An additional 5 mL DMSO wash was also drawn into the syringe. The CPG-nucleoside mixture was mixed for 1.5 h, then the CPG washed with 5 volumes of anhydrous acetonitrile. Unreacted CPG amino groups were acetylated by standard capping solutions (PE Applied Biosystems, Foster City, Calif.) for 2 min. The CPG was again washed with 5 volumes of acetonitrile and 5 volumes of CH$_2$Cl$_2$. Nucleoside loading was determined to be approximately 5 μmole/g by standard trityl assay.

EXAMPLE 19

Solid Phase Synthesis of Oligo-2'-fluoronucleotide N3'→P5' Phosphoramidates

Figure 4:
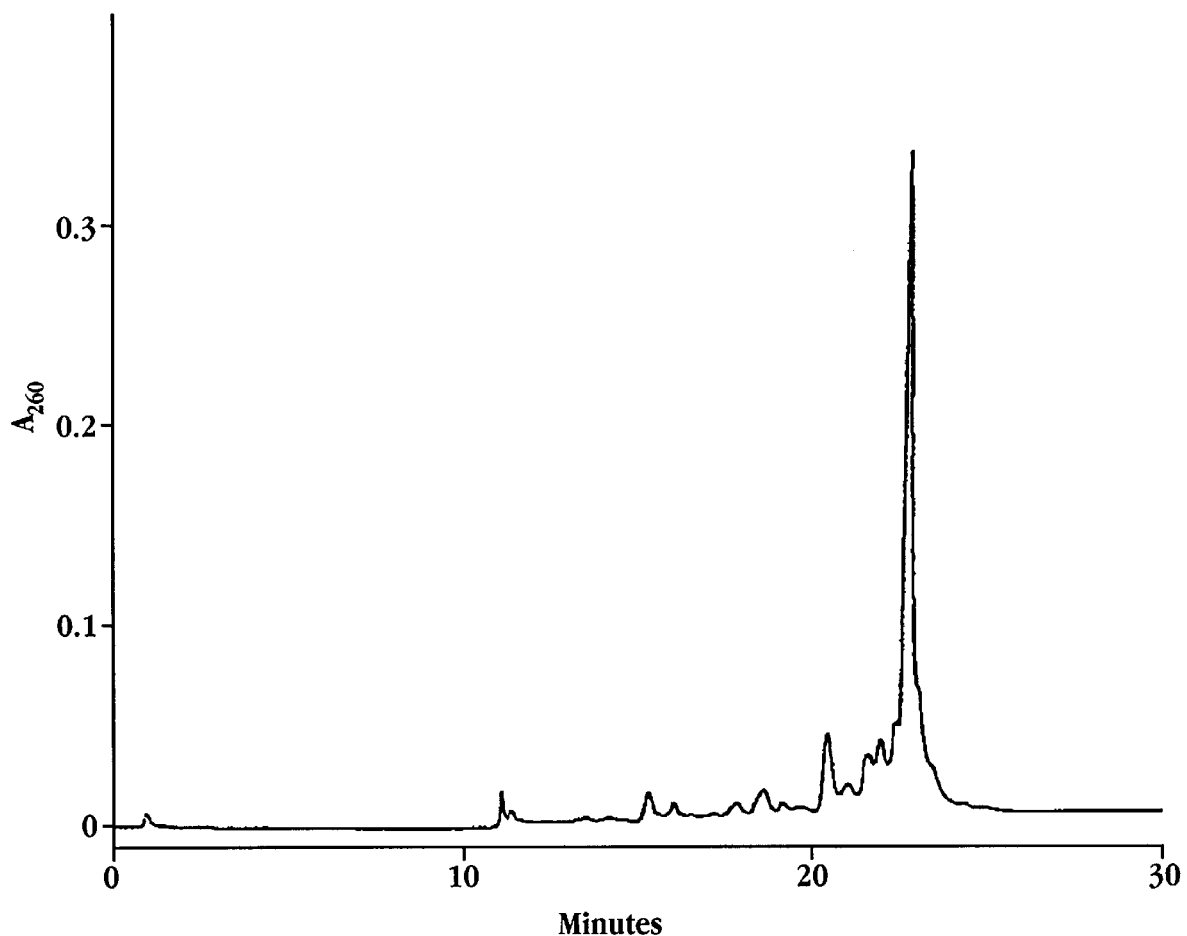
FIG. 4 is an ion exchange HPLC chromatogram of the crude reaction mixture from synthesis of an oligo-2'-fluoronucleoside N3'→P5' phosphoramidate of Example 19.

Oligo-2'-fluoronucleotide N3'->P5' phosphoramidates were synthesized on solid phase supports using phosphoramidite monomers of Schemes V and VI. Compounds 22–25 (Table 1) were synthesized by way of phosphoramidite monomers. The average coupling efficiency as determined by released MMT-cation assay was ~94% with single coupling per cycle and ~96% with double application of Step 2 per synthetic cycle. A representative IE HPLC profile of a crude oligomer synthesis is shown in FIG. 4.

Uniformly modified oligo-2'-fluoronucleotide N3'→P5' phosphoramidates were prepared by amidite transfer reaction on an ABI 380B synthesizer using the following protocol:

1) detritylation, 5% dichloroacetic acid in dichloromethane, 1 min.

2) coupling, 0.1M phosphoramidite 2u or 2c (Scheme V or VI, respectively) and 0.45M tetrazole in acetonitrile, 3 min.

3) oxidation, 0.1M iodine in tetrahydrofuran/pyridine/water, 10/10/1, v/v/v, 1 min.

4) capping, acetylation of unreacted 3'-amino groups by standard PE Applied Biosystems (Foster City, Calif.) capping solutions, 30 sec.

Chemical steps within the cycle were followed by acetonitrile washings and flushings with dry argon for 0.2–0.4 min. After cleavage from the solid support and deprotection with concentrated aqueous ammonia, 1–1.5 h, 55° C., oligonucleotides were analyzed and purified by IE HPLC. Oligonucleotides were desalted on Pharmacia NAP-5 or NAP-10 gel filtration columns immediately after purification and stored frozen or lyophilized at –18° C.

Preparation of the 5'-phosphorylated oligonucleotides was done upon sulfone-derivatized CPG, e.g. Gryaznov, S. M.; Letsinger, R. L. *Nucleic Acids Res.* 1993, 21, 1403–1408.

Dionex DX300 or DX500 systems were used for IE analysis and purification of -oligonucleotides. A Pharmacia MonoQ 10/10 column was used for analysis and purification of crude oligomers, eluted with a 2% per minute gradient of 1.5M NaCl in 10 mM NaOH. A Dionex NucleoPac PA100 column, eluted with a 1.5% per minute gradient of 1.5M NaCl in 10 mM NaOH was used for all other IE HPLC analysis. A Hewlett Packard Hypersil ODS, 5μ column on a Waters HPLC system was used for RP HPLC, with a 1% per minute gradient of acetonitrile in 0.1M triethylammonium acetate, pH 7.0.

NMR spectra were recorded on a Bruker DRX-400 spectrometer. Chemical shifts are reported relative to TMS, CCl$_3$F, and H$_3$PO$_4$, for $^1$H, $^{19}$F, and $^{31}$P spectra, respectively.

Thin layer chromatography (TLC) was performed on Whatman polyester-backed silica gel plates with methanol/dichloromethane eluents.

Acid hydrolysis of 0.17 $OD_{260}$ of the dimer $dU^f_{np}T$ was done in 25 μL of 64% acetic acid, 2 h at 55° C., and the reaction mixture was analyzed by RP HPLC. Approximately 83% of the dimer, retention time (Rt) 15.0 min, was hydrolyzed to mainly 5'-thymidylic acid, Rt 10.6 min, and 2'-fluor-3'-aminouridine, Rt 11.2 min, as were identified by co-injection with authentic standards. Also, ~7.5% of thymidine, Rt 12.1 min, was found in the reaction mixture.

butyldimethylsilyl)-$N^2$-isobutyryl-$O^6$-diphenylcarbamoyl-3'-(trityl)amino-2',3'-dideoxyguanosine, $2g^{dpc}$ (43.5 g, 49.0 mmol) was dissolved in $CH_2Cl_2$ (200 mL), and pyridine (25 mL) was added. Triethylamine trihydrofluoride (49.8 mL, 305.8 mmol) was added, followed by a $CH_2Cl_2$ rinse (25 mL), and the reaction mixture was stirred at RT under argon for 20 h. The reaction mixture was diluted with $CH_2Cl_2$ (600 mL) and extracted with $H_2O$ (2×400 mL). The first aqueous layer was back-extracted with $CH_2Cl_2$ (50 mL), and the combined organics were dried over $Na_2SO_4$, filtered, and concentrated in vacuo. The residue was redissolved in $CH_2Cl_2$, azeotroped with toluene (3×) to remove traces of

TABLE 1

Oligonucleotides and $T_m$ values of their duplexes.

| Expt | Oligonucleotide[a] | No. | SEQ ID NO: | $T_m$°C[b] DNA[c] | $T_m$°C[b] RNA[c] |
|---|---|---|---|---|---|
| 1 | UUUUUUUUUT | 18 | 8 | 16.7;24.6 | 17.9;20.3 |
| 2 | $U_{np}U_{np}U_{np}U_{np}U_{np}U_{np}U_{np}U_{np}U_{np}T$ | 19 | 8 | 18.5;38.2 | 38.1;47.2 |
| 3 | $U_{np}U_{np}U_{np}U_{np}U^f_{np}U_{np}U_{np}U_{np}U_{np}T$ | 20 | 8 | 20.0;41.0 | 40.1;49.3 |
| 4 | $U_{np}U_{np}U_{np}U^f_{np}U^f_{np}U_{np}U_{np}U_{np}U_{np}T$ | 21 | 8 | 23.4;44.6 | 44.5;52.7 |
| 5 | $pU^f_{np}U^f_{np}U^f_{np}U^f_{np}U^f_{np}U^f_{np}U^f_{np}U^f_{np}U^f_{np}T$ | 22 | 8 | 34.6;63.0 | 55.2;64.6 |
| 6 | $pU^f_{np}U^f_{np}U^f_{np}U^f_{np}U^f_{np}U^f_{np}U^f_{np}U^f_{np}U^f_{np}U_n$ | 23 | 9 | 39.5;63.2 | 56.4;64.0 |
| 7 | $C_{np}U_{np}U_{np}C_{np}U_{np}U_{np}C_{np}C_{np}U_{np}U_{np}A$ | 24 | 10 | 44.2;— | 66.0;— |
| 8 | $C^f_{np}U^f_{np}U^f_{np}C^f_{np}U^f_{np}U^f_{np}C^f_{np}C^f_{np}U^f_{np}U^f_{np}A$ | 25 | 10 | 56.9;— | 81.6;— |

[a]All 2'-deoxy compounds; np, f, p, and n represent 3'NHP(O)(O)O–5' internucleoside link, 2'-fluorine, 5'-phosphate, and 3'-amine, respectively;
[b]$T_m$ was determined with 3 μM of oligonucleotides; first values were determined in 10 mM sodium phosphate, 150 mM sodium chloride, pH 7.04; second values were determined in same buffer containing an additional 10 mM magnesium chloride; dashes are for not determined $T_m$s.
[c]complementary target; poly(dA) or poly(rA) for experiments 1–6, d(ATAAGGAAGAAGC) or r(AUAAGGAAGAAGC) for experiments 7, 8.

EXAMPLE 20

Preparation of $N^2$-Isobutyryl-$O^6$-diphenylcarbamoyl-3'-(trityl)amino-2',3'-dideoxyguanosine-5'-phosphoramidite Monomers The synthesis of $N^2$-isobutyryl-$O^6$-diphenylcarbamoyl-3'-(trityl)amino-2',3'-dideoxyguanosine-5'-(2-cyanoethyl N,N-diisopropyl) phosphoramidite, $4g^{dpc}$ is outlined in Scheme VII.

5'-O-(tert-Butyldimethylsilyl)-$N^2$-isobutyryl-$O^6$-diphenylcarbamoyl-3'-(trityl)amino-2',3'-dideoxyguanosine, $2g^{dpc}$. To 5'-O-(tert-butyldimethylsilyl)-$N^2$-isobutyryl-3'-(trityl)amino-2',3'-dideoxyguanosine, 2g (30.3 g, 43.7 mmol) was added anhydrous pyridine (90 mL), N,N-diisopropylethylamine (11.4 mL, 65.6 mmol), and diphenylcarbamyl chloride (11.1 g, 48.1 mmol) under argon. After stirring for 1.5 h at RT, the intensely red/purple reaction mixture was concentrated in vacuo. The residue was redissolved in $CH_2Cl_2$ (600 mL), extracted with $H_2O$ (2×400 mL) and satd. aq. NaCl (400 mL), dried over $Na_2SO_4$, filtered, and concentrated in vacuo. The residue was then redissolved in $CH_2Cl_2$ and azeotroped with toluene (3×). This afforded >100% yield (43.8 g) of impure 5'-O-(tert-butyldimethylsilyl)-$N^2$-isobutyryl-$O^6$-diphenylcarbamoyl-3'-(trityl)amino-2',3'-dideoxyguanosine, $_2g^{dpc}$ which was generally taken on directly to desilylation, although it could also be purified on silica. $^1$H NMR (CDCl$_3$/TMS): δ 8.03 (1H, s), 7.90 (1H, br s, exchanges with $D_2O$), 7.55 (6H, d, J=7.63 Hz), 7.24–7.50 (16H, mm), 7.21 (3H, t, J=7.22 Hz), 6.29 (1H, t, J=6.07 Hz), 3.89 (1H, m), 3.75 (2H, ABX, $J_{AB}$=11.25 Hz), 3.49 (1H, br m), 3.01 (1H, br m), 2.77 (1H, septet, J=6.78 Hz), 2.00–2.10 (br s, exchanges with $D_2O$), 1.65–1.75 (2H, m), 1.28 (6H, d, J=6.64 Hz), 0.83 (9H, s), –0.01 (3H, s), –0.02 (3H, s).

$N^2$-Isobutyryl-$O^6$-diphenylcarbamoyl-3'-(trityl)amino-2',3'-dideoxyguanosine, $3g^{dpc}$. Crude 5'-O-(tert-butyldimethylsilyl)-$N^2$-isobutyryl-$O^6$-diphenylcarbamoyl-3'-(trityl)amino-2',3'-dideoxyguanosine, $2g^{dpc}$ (43.5 g, 49.0 mmol) was dissolved in $CH_2Cl_2$ (200 mL), and pyridine (25 mL) was added. Triethylamine trihydrofluoride (49.8 mL, 305.8 mmol) was added, followed by a $CH_2Cl_2$ rinse (25 mL), and the reaction mixture was stirred at RT under argon for 20 h. [continuation]

pyridine, and purified on silica (packed in 0.5% $Et_3N$ in 70:30 EtOAc/hexane and eluted with 70:30 EtOAc/hexane) to afford 27.6 g of semi-pure product. The column was repeated and afforded a 56.5% yield (21.4 g, 27.7 mmol) of pure $N^2$-isobutyryl-$O^6$-diphenylcarbamoyl-3'-(trityl)amino-2',3'-dideoxyguanosine, $3g^{dpc}$. $^1$H NMR (CDCl$_3$/TMS): δ 7.95 (1H, s), 7.84 (1H, br s, exchanges with $D_2O$), 7.55 (6H, d, J=7.85 Hz), 7.25–7.45 (16H, mm), 7.21 (3H, t, J=7.25 Hz), 6.15 (1H, t, J=6.31 Hz), 3.77–3.87 (2H, br m), 3.69 (1H, m), 3.62 (1H, m), 3.19 (1H, m), 2.80 (1H, septet, J=6.86 Hz), 1.92–2.05 (2H, mm, 1H exchanges with $D_2O$), 1.65 (1H, m), 1.24 (6H, d, J=6.86 Hz). HRMS (FAB$^+$): calcd for [M+Cs]$^+$, 906.2380, observed 906.2350. Anal. calcd for $C_{46}H_{43}N_7O_5$: C, 71.39; H, 5.60; N, 12.67; observed: C, 69.98; H, 5.65; N, 12.25.

$N^2$-isobutyryl-$O^6$-diphenylcarbamoyl-3'-(trityl)amino-2',3'-dideoxyguanosine-5'-(2-cyanoethyl N,N-diisopropyl) phosphoramidite, $4g^{dpc}$. To $N^2$-isobutyryl-$O^6$-diphenylcarbamoyl-3'-(trityl)amino-2',3'-dideoxyguanosine, $3g^{dpc}$ (0.88 g, 1.14 mmol), previously aeotroped 2 times from $CH_3CN$, in 5 mL $CH_2Cl_2$ under argon was added 0.3 mL (1.71 mmol) of N,N-diisopropylethylamine and 0.28 mL (1.25 mmol) of 2-cyanoethyl N,N-diisopropylchlorophosphoramidite. After stirring for 15 min the reaction was diluted with $CH_2Cl_2$ and extracted with saturated aq. NaHCO$_3$ and saturated aq. NaCl. The organic layer was dried (Na$_2$SO$_4$), filtered and concetrated in vacuo. The crude product was purified on SiO$_2$ (60% ethyl acetate/2% triethylamine/hexane) and gave 0.97 g (87.5% yield) of pure $N^2$-isobutyryl-$O^6$-diphenylcarbamoyl-3'-(trityl)amino-2',3'-dideoxyguanosine-5'-(2-cyanoethyl N,N-diisopropyl) phosphoramidite, $4g^{dpc}$. $^{31}$p NMR (CD$_3$CN) δ 148.8, 149.4.

Scheme VII

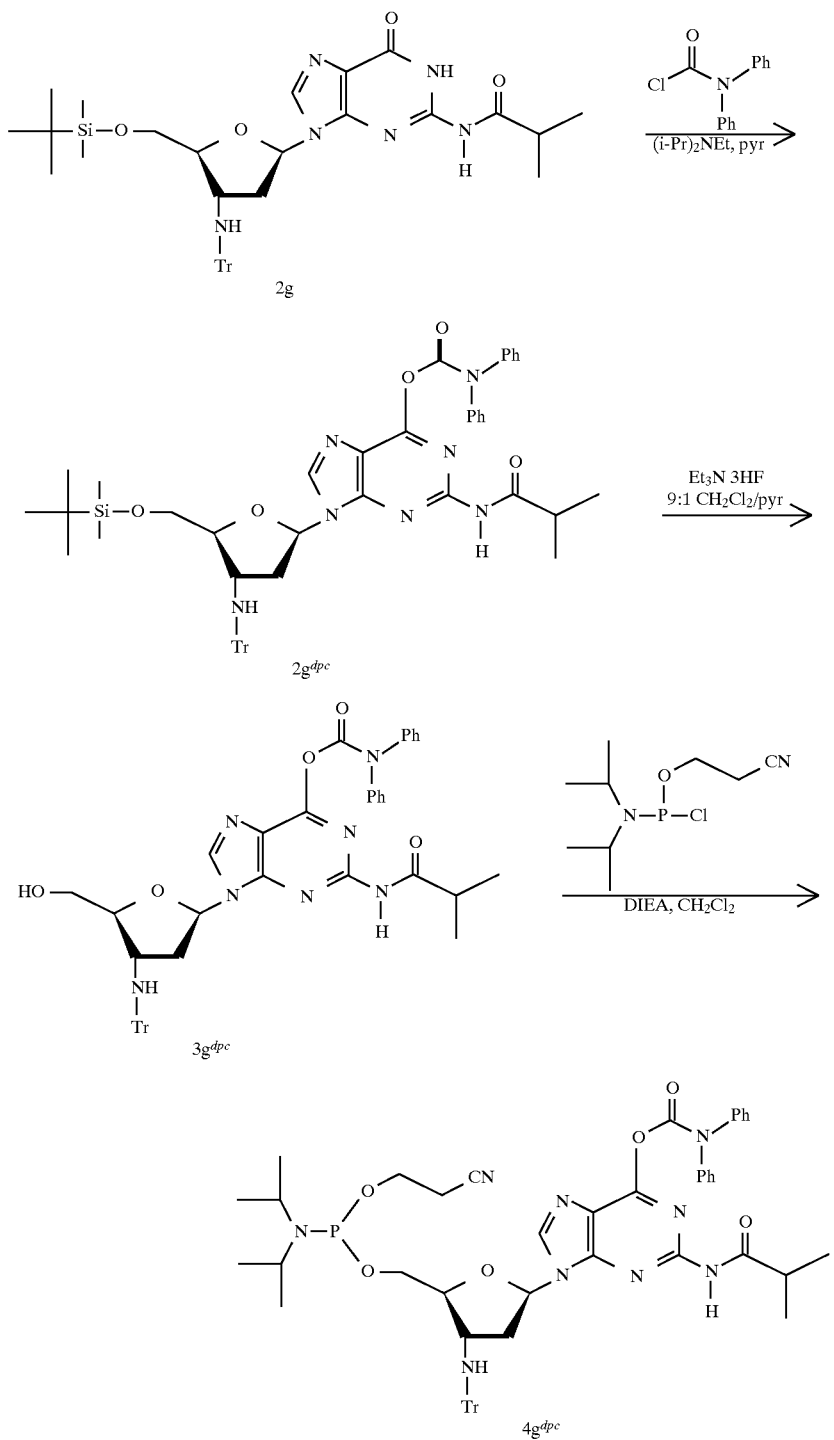

EXAMPLE 21

Preparation of 2-cyanoethyl 2,6-cis-dimethylpiperidinechlorophosphoramidite 2-Cyanoethylphosphorodichloridite. To a solution of phosphorus trichloride (500 mL, 5.73 mol) in 250 mL of acetonitrile was added dropwise at room temperature, with stirring and bubbling of argon, a solution of 3-hydroxypropionitrile (47 mL, 0.69 mol) in 250 mL of acetonitrile. The solution was stirred 15 minutes at room temperature, with absorption of evolving HCl into a solution of 10% aqueous KOH, and then concentrated on the rotary evaporator and then filtered into a distillation flask. The 2-cyanoethylphosphorodichloridite (88.5 g, 75.7%) distilled as a colorless liquid at 78°–80° C., 1.0 mmHg. $^{31}$P NMR (CDCl$_3$) δ 180.3.

2-Cyanoethyl 2,6-cis-dimethylpiperidinechlorophosphor-amidite. To a solution of 2-cyanoethylphosphorodichloridite (35.0 g, 203.6 mmol) in 300 mL toluene:hexane (1:4, v/v) was added cis-2,6-dimethylpiperidine (55 mL, 408.1 mmol) dropwise at 4° C. The reaction was stirred for 2 hours at room temperature, then filtered and the solid washed with 40 mL of toluene:hexane (1:4, v/v). The filtrate was concentrated on the rotary evaporator. To the resultant oil was added 5 mL of $CH_2Cl_2$ and 300 mL of hexane which resulted in crystallization of the product. After the crystallization was complete (4° C., overnight), the 2-cyanoethyl 2,6-cis-dimethylpiperidinechlorophosphoramidite was filtered under argon, crushed with a spatula, washed with 100 mL of hexane:$CH_2Cl_2$ (100:3, v/v), and dried in vacuo. The mother liquor was concentrated and was recrystallized to give a second crop of product. The combined products yielded 38.8 g (76.5%) of pale yellow crystals. $^{31}$P NMR ($CDCl_3$) δ 172.7.

EXAMPLE 22

General Method for the Synthesis of Dimethylpiperidinyl Phosphoramidite Monomers—Synthesis of 3'-(trityl)amino-5'-(2,6-cis-dimethylpiperidinyl-2-cyanoethyl) phosphoramidite-N2-isobutyryl-O6-diphenylcarbamoyl-2',3'-dideoxyguanosine To 10.0 g (12.92 mmol) of 3'(tritylamino)-$N^2$-isobutyryl-O6-diphenylcarbamoyl-2',3'-dideoxyguanosine (previously azeotroped 2 times from $CH_3CN$) and 3.9 mL (25.84 mmol) of DBU in 40 mL of $CH_2Cl_2$ was added, with stirring, a solution of 2-cyanoethyl 2,6-cis-dimethylpiperidine-chlorophosphoramidite (3.86 g, 15.5 mmol) in 10 mL of $CH_2Cl_2$, all under an argon atmosphere. The reaction mixture was stirred for 15 minutes at ambient temperature. The reaction mixture was diluted with $CH_2Cl_2$ and extracted with saturated aqueous sodium bicarbonate and then with brine. The solution was dried with $Na_2SO_4$, filtered, and dried by rotary evaporation to yield 14.5 g of crude product. The crude product was purified by $SiO_2$ chromatography and eluted with a gradient of 50–60% Ethyl Acetate, 3% TEA, in hexane, to yield, after concentrating by rotary evaporation and drying in vacuo, 10.15 g (79.7%) of pure product. $^{31}$P NMR ($CD_3CN$) δ 149.49, 148.91.

EXAMPLE 23

10-μmol Scale Synthesis of oligo-2'-deoxynucleoside N3'→P5' Phosphoramidates with a Terminal 3'-hydroxyl Group (5'-AAC-GTT-GAG-GGG-CAT-OH-3'): Use of Hydrogen Peroxide Oxidation, O6-diphenylcarbamoyl Protected G Monomer, Isobutyric Anhydride Capping, and Dimethylpiperidinyl Phosphoramidite Monomers The same general procedure described in Example 14 was used, with the following exceptions:

3'-tritylamino-2',3'-dideoxy-5'-dimethylpiperidinyl (cyanoethyl) phosphoramidites were used for all of the monomer couplings except the terminal 3'-T. The G monomer was protected at the 0–6 position with a diphenylcarbamoyl group in addition to its N-2 isobutyryl protection. The following cycle was used for all but the 3'-terminal T cycle:

1) Detritylation of the trityl group from the 3'-amino group of the support-bound (oligo)nucleotide, as in example 14.

The solid support was then washed 10 times with a series of alternating washes from the bottom of the reaction vessel as well as from the top with vortexing and draining.

2) Coupling of the resulting free amine (presumably as its dichloroacetate salt) with the 3'-(trityl)aminonucleoside-5'-phosphoramidite monomer was performed using an initial delivery of monomer (0.1M in dry acetonitrile) to the reaction vessel followed by the delivery of 0.166M tetrazole in dry acetonitrile. 3.6 equivalents of monomer and 9 equivalents of tetrazole were used. The coupling mixture was then vortexed for 5 minutes, and the reaction vessel was drained.

The solid support was then washed with a series of 6 washes with a solution of 20% dry pyridine in dry acetonitrile with vortexing.

3) The resulting internucleotide phosphoramidite linkage was oxidized with a solution of 1.5% hyrogen peroxide, 3.5% water, 20% pyridine, and 75% tetrahydrofuran. The reaction vessel was vortexed for 2 minutes and drained.

The solid support was washed 10 times with a series of alternating acetonitrile washes from the bottom of the reaction vessel as well as from the top with vortexing and draining.

4) The unreacted 3'-amino groups were capped for 2 minutes with vortexing and drained. The capping reagents were added alternately, and in equal volumes. One capping reagent was a 1:1:8 (v/v/v) mixture of isobutyric anhydride: lutidine: tetrahydrofuran. The other reagent was a solution of 1-methylimidizole in tetrahydrofuran (PE/Applied Biosystems, Foster City, Calif.).

The solid support was washed 10 times with a series of alternating acetonitrile washes from the bottom of the reaction vessel as well as from the top with vortexing and draining.

For the 3'-terminal T coupling a 0.1M solution of 3'-DMT-T-5'-diisopropylamino (cyanoethyl) phosphoramidite (Glenn Research) in dry acetonitrile and a 0.5M solution of tetrazole in dry acetonitrile were used. 10 equivalents of monomer and 25 equivalents of tetrazole were used for each coupling step. This last cycle which involves the addition of the diisopropylaminophosphoramidite monomer was the same as the cycle outlined above, except that after steps 2 and 3 were completed, they were repeated again (couple, oxidation, couple, oxidation) before going on to step 4. Step 4 was followed, after washing with acetonitrile as above, with a final detritylation step and acetonitrile wash.

Figure 5:
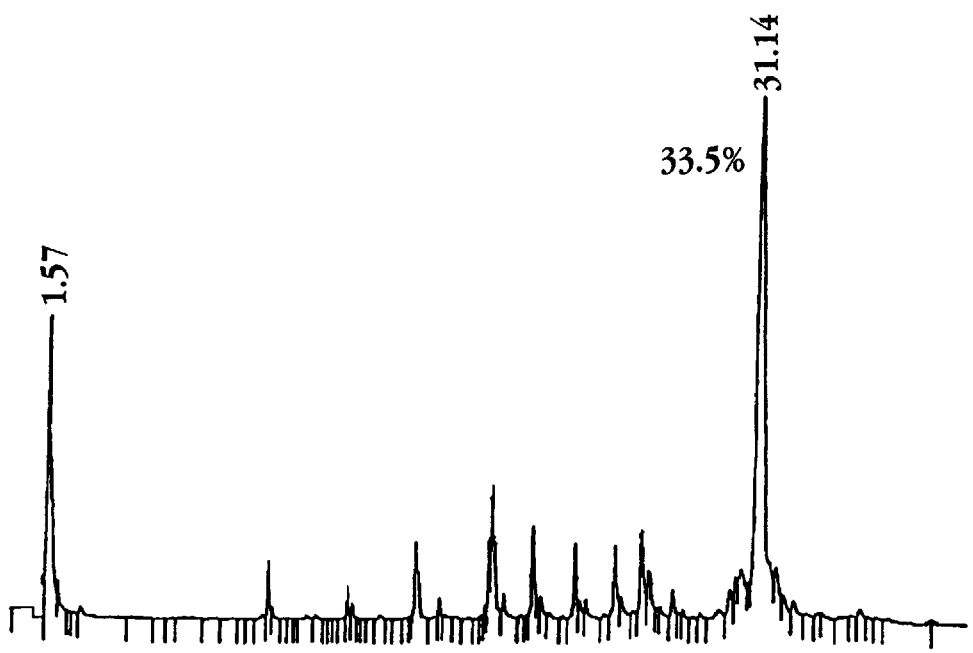
FIG. 5 is an ion exchange HPLC chromatogram of the crude reaction mixture from synthesis of an oligodeoxynucleoside N3'→P5' phosphoramidate of Example 23.

Upon completion of the synthesis, the 3'-deprotected oligonucleotide was cleaved from the support and deprotected with concentrated aqueous ammonia at 55° for 12 hours. The solution was buffered to 0.01M NaOH and the ammonia removed under vacuum. The anion-exchange chromatogram of the crude oligonucleotide appears in FIG. 5.

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

GGCCAAAAAG CCACTAT 17

( 2 ) INFORMATION FOR SEQ ID NO: 2:

( i ) SEQUENCE CHARACTERISTICS:
        ( A ) LENGTH: 11 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

AAGCCTTTAT C 11

( 2 ) INFORMATION FOR SEQ ID NO: 3:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

TTTTTTTTTT TTTTT 15

( 2 ) INFORMATION FOR SEQ ID NO: 4:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

AAAAAAAAAA AAAAA 15

( 2 ) INFORMATION FOR SEQ ID NO: 5:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

AACGAGTTGG GGCAT 15

( 2 ) INFORMATION FOR SEQ ID NO: 6:

( i ) SEQUENCE CHARACTERISTICS:
        ( A ) LENGTH: 11 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TTCTCTCTCT A 11

( 2 ) INFORMATION FOR SEQ ID NO: 7:

```
        ( i ) SEQUENCE CHARACTERISTICS:
                ( A ) LENGTH: 15 nucleotides
                ( B ) TYPE: nucleic acid
                ( C ) STRANDEDNESS: single
                ( D ) TOPOLOGY: linear ( x i ) SEQUENCE DESCRIPTION: SEQ ID NO: 7:

A A C A T G G A G A   G C G T C                                                                                  1 5

( 2 ) INFORMATION FOR SEQ ID NO: 8:

( i ) SEQUENCE CHARACTERISTICS:
                ( A ) LENGTH: 10 nucleotides
                ( B ) TYPE: nucleic acid
                ( C ) STRANDEDNESS: single
                ( D ) TOPOLOGY: linear ( x i ) SEQUENCE DESCRIPTION: SEQ ID NO: 8:

U U U U U U U U U T                                                                                              1 0

( 2 ) INFORMATION FOR SEQ ID NO: 9:

( i ) SEQUENCE CHARACTERISTICS:
                ( A ) LENGTH: 10 nucleotides
                ( B ) TYPE: nucleic acid
                ( C ) STRANDEDNESS: single
                ( D ) TOPOLOGY: linear ( x i ) SEQUENCE DESCRIPTION: SEQ ID NO: 9:

U U U U U U U U U U                                                                                              1 0

( 2 ) INFORMATION FOR SEQ ID NO: 10:

( i ) SEQUENCE CHARACTERISTICS:
                ( A ) LENGTH: 11 nucleotides
                ( B ) TYPE: nucleic acid
                ( C ) STRANDEDNESS: single
                ( D ) TOPOLOGY: linear ( x i ) SEQUENCE DESCRIPTION: SEQ ID NO: 10:

C U U C U U C C U U   A                                                                                          1 1
```

We claim:

1. A compound of the formula:

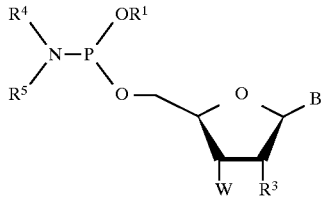

wherein:
B is pyrimidine, purine, or an analog thereof;
$R^1$ is a phosphate protecting group;
W is —$NHR^2$, where $R^2$ is an amino protecting group and;
$R^3$ is hydrogen, hydroxyl, fluoro or —OR', where R' is alkyl having from 1 to 3 carbon atoms or a hydroxyl protecting group; and
$R^4$ and $R^5$ together with the nitrogen to which they are attached form an alkylamino- or arylamino leaving group having up to 40 atoms selected from the group consisting of carbon, oxygen, sulfur, and nitrogen.

2. The compound of claim 1 wherein $R^3$ is hydrogen; and $R^4$ and $R^5$ taken separately are alkyl, aralkyl, cycloalkyl, or cycloalkylalkyl having a combined total of from 6 to 20 carbon atoms.

3. The compound of claim 2 wherein R' is methyl, β-cyanoethyl, or 4-nitrophenylethyl; $R^2$ is triphenylmethyl; $R^7$ is di-p-anisylphenylmethyl; and $R^4$ and $R^5$ taken separately are isopropyl, sec-butyl, isobutyl, t-butyl, cyclohexyl, or 2-ethylhexyl.

4. The compound of claim 3 wherein B is $O^6$-diphenylcarbamoyl-$N^2$-protected-guanine.

5. The compound of claim 4 consisting of $N^2$-isobutyryl-$O^6$-diphenylcarbamoyl-3'-(trityl)amino-2',3'-dideoxyguanosine-5'-(2-cyanoethyl N,N-diisopropyl) phosphoramidite.

6. The compound of claim 1 wherein $R^3$ is hydrogen and wherein $R^4$ and $R^5$ taken together form an alkylene chain containing up to 6 carbon atoms in the principal chain and a total of from 4 to 12 carbon atoms.

7. The compound of claim 1 wherein $R^3$ is hydrogen and wherein $R^4$ and $R^5$ taken together with the nitrogen to which they are attached form a saturated nitrogen heterocycle having up to 10 carbon atoms or heteroatoms in the principal chain and a total of from 4 to 20 carbon atoms or heteroatoms altogether, such that $R^4$ and $R^5$ taken together with the nitrogen to which they are attached contain up to three heteroatoms selected from the group consisting of nitrogen, oxygen, and sulfur.

8. The compound of claim 7 wherein $R^1$ is methyl, β-cyanoethyl, or 4-nitrophenylethyl; $R^2$ is triphenylmethyl; and $R^4$ and $R^5$ taken together and with the nitrogen to which they are attached are dimethylpipiridinyl, pyrrolidinyl, dimethylmorpholino, tetramethylmorpholino, dimethylpyrrolidinyl, tetramethylpyrrolidinyl, or tetramethylpiperidinyl.

\* \* \* \* \*